US006677344B2

(12) United States Patent
Fukami et al.

(10) Patent No.: US 6,677,344 B2
(45) Date of Patent: Jan. 13, 2004

(54) CHYMASE INHIBITOR FOR THE TREATMENT OF EOSINOPHILIA

(75) Inventors: Harukazu Fukami, Kyoto (JP); Naohiro Watanabe, Tokyo (JP)

(73) Assignee: Daiichi Suntory Pharma Co., Ltd., Tokyo (JP)

( * ) Notice: Subject to any disclaimer, the term of this patent is extended or adjusted under 35 U.S.C. 154(b) by 0 days.

(21) Appl. No.: 09/959,358

(22) PCT Filed: Feb. 22, 2001

(86) PCT No.: PCT/JP01/01322

§ 371 (c)(1),
(2), (4) Date: Oct. 22, 2001

(87) PCT Pub. No.: WO01/62293

PCT Pub. Date: Aug. 30, 2001

(65) Prior Publication Data

US 2002/0187989 A1 Dec. 12, 2002

(30) Foreign Application Priority Data

Feb. 22, 2000 (JP) ............................................ 2000-50487

(51) Int. Cl.[7] ..................... A61K 31/517; A61K 31/536
(52) U.S. Cl. ................................ 514/266.3; 514/266.2; 514/266.1; 514/230.5
(58) Field of Search .......................... 514/259, 230.5, 514/266.1, 266.2, 266.3

(56) References Cited

U.S. PATENT DOCUMENTS

| 5,691,335 A | 11/1997 | Fukami et al. ........... 514/235.8 |
| 5,814,631 A | 9/1998 | Fukami et al. ........... 514/234.5 |

FOREIGN PATENT DOCUMENTS

| EP | 713876 A1 | 5/1996 |
| EP | 795548 A1 | 9/1997 |
| EP | 936216 A1 | 8/1999 |
| HU | 218381 | 5/1996 |
| JP | 63-51335 A | 3/1986 |
| JP | 5-294930 A | 11/1993 |
| JP | 10-87493 A | 4/1997 |
| JP | 10-101666 A | 4/1998 |
| JP | 10-245384 A | 9/1998 |
| JP | 11-246437 A | 9/1999 |
| JP | 2001-97946 A | 4/2001 |
| WO | 93/03625 A1 | 3/1993 |
| WO | 93/25574 A1 | 12/1993 |
| WO | 94/26722 | 11/1994 |
| WO | 96/04248 A1 | 2/1996 |
| WO | 96/33974 A1 | 10/1996 |
| WO | 96/39373 A1 | 12/1996 |
| WO | 9809949 | * 3/1998 |
| WO | 98/18794 A1 | 5/1998 |
| WO | 99/41277 A1 | 8/1999 |
| WO | 00/10982 A1 | 3/2000 |
| WO | 01/32214 A1 | 5/2001 |
| WO | 01/62292 A1 | 8/2001 |
| WO | 01/62294 A1 | 8/2001 |

OTHER PUBLICATIONS

Shaoheng He, et al, "Human mast cell chymase induces the accumulation of neutrophils, eosinophils and other inflammatory cells in vivo," British Journal of Pharmacology, vol. 125, 1998, pp. 1491–1500.

Claudia Lützelschwab, et al, "A kinetic analysis of the expression of mast cell protease mRNA in the intestines of *Nippostrongylus brasiliensis*–infected rats," Eur. J. Immunol., vol. 28, 1998, pp. 3730–3737.

J.M. Wastling, et al, "Constitutive expression of mouse mast cell protease–1 in normal BALB/c mice and its up–regulation during intestinal nematode infection," Immunology, vol. 90, 1997, pp. 308–313.

Hitoshi Mizutani, et al, "Rapid and Specific Conversion of Precursor Interleukin 1β (IL–1β) to an Active IL–1 Species by Human Mast Cell Chymase," J. Exp. Med., vol. 174, Oct. 1991, pp. 821–825.

Jack Longley, et al, "Chymase cleavage of stem cell factor yields a bioactive, soluble product," Proc. Natl. Acad. Sci. USA, vol. 94, Aug. 1997, pp. 9017–9021.

Cory M. Hogaboam, et al, "Intestinal platelet–activating factor synthesis during *Nippostrongylus brasiliensis* infection in the rat," Journal of Lipid Mediators, vol. 4, 1991, pp. 211–224.

Naohiro Watanabe, et al, "Protective immunity and eosinophilia in IgE–deficient SJA/9 mice infected with *Nippostrongylus brasiliensis* and *Trichinella spiralis*," Proc. Natl. Acad. Sci. USA, vol. 85, Jun. 1988, pp. 4460–4462.

Yong Huang, et al, "The Involvement of CD80 and CD86 Costimulatory Molecules in the Induction of Eosinophilia in Mice Infected with *Nipponstrongylus brasiliensis*," Int. Arch. Allergy Immunol, 117 (Suppl 1), 1998, pp. 2–4.

* cited by examiner

Primary Examiner—Phyllis G. Spivack
(74) Attorney, Agent, or Firm—Burns Doane Swecker & Mathis LLP

(57) ABSTRACT

A chymase inhibitor for the prevention or treatment of diseases involving an increase of eosinophils, as the effective ingredient, is disclosed, suppress the progress of the disease and to prevent progression of complications, wherein the chymase inhibitor is a quinazoline derivative having the formula (I):

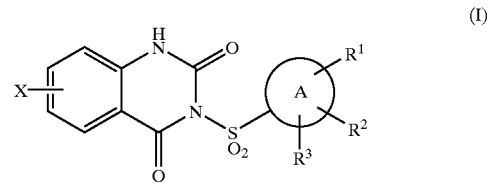

(I)

wherein X, $R^1$, $R^2$ and $R^3$ are herein defined, or a pharmaceutically acceptable salt thereof.

54 Claims, No Drawings

CHYMASE INHIBITOR FOR THE TREATMENT OF EOSINOPHILIA

TECHNICAL FIELD

The present invention relates to a medicament for the prevention or treatment of a disease accompanied with an increase in eosinophils, a pharmaceutical composition for the prevention or treatment of allergic diseases, and a medicament for suppressing an increase in eosinophils.

BACKGROUND ART

Eosinophils are granulocytes comprising 1 to 3% of peripheral blood leukocytes and are believed to be involved in allergic dermatitis or bronchial asthma and other allergic diseases or parasitic infections and other conditions (*Eur. Respir. J. Suppl.* 22, 109s, 1996). A disease condition where the ratio of eosinophils in the peripheral blood increases to 6% or more is called "eosinophilia". This condition is also observed in various skin disease (e.g., herpes, cnidosis, psoriasis, eczema), hematological diseases (e.g., myelocytic leukemia, pernicious anemia), infectious diseases, (e.g., cholera, malaria), and, bone diseases (e.g., sarcoma, rickets, myelitis), etc. in addition to the above diseases.

Eosinophils have granules containing basic cytotoxic proteins called MBP (major basic proteins), ECP (eosinophil cationic proteins), EDN (eosinophil-derived neurotoxins), etc. (*Pharmacol. Rev.* 51, 213, 1999). When allergic reactions or inflammation reactions occur, it is believed that eosinophils migrate to and infiltrate into these inflammatory areas, then cause degranulation and release these cytotoxic proteins so as to exacerbate these reactions (*Trends Pharmacol. Sci.* 16, 418, 1995). The major cytokines involved in the proliferation and differentiation of eosinophils are IL-5 (Interleukin-5), IL-3 (Interleukin-3), GM-CSF, etc. Further, RANTES or eotaxins and other chemokines play an important role in the accumulation of eosinophils in inflamed sites (*Int. Arch. Allerg. Immunol.* 113, 196, 1997, *J. Leukoc. Biol.* 59, 1, 1996).

It has been reported that various substances such as steroids (*Br. J. Pharmacol.* 101, 821, 1990), phosphodiesterase inhibitors (*J. Pharmacol. Exp. Ther.* 278, 1356, 1996), cyclosporins (*Pharmacol. Rev.* 51, 213, 1999), and tacrolimus (*Br. J. Pharmacol.* 120, 130, 1997) inhibit the functions of eosinophils, but they are not sufficiently satisfactory in terms of efficacy, specificity, side effects, etc. In addition, several anti-allergic agents are known to suppress the functions of eosinophils (*Pharmacol. Rev.* 51, 213, 1999), but the main mechanisms of their action is an antagonist action against histamine acceptors. It is unclear to what extent this action on eosinophils is involved in the clinical effects of these medicaments. That is, the relationship between the proliferation or function of eosinophils and the diseases including eosinophilia, allergic diseases and inflammation has not yet been elucidated.

On the other hand, chymase is a serine protease stored in mast cell granules, and widely present in tissues such as the skin, heart, vascular walls, intestines, etc. (*Mast Cell Proteases in Immunology and Biology; Caughey*, G. H., Ed; Marcel Dekker, Inc.; New York, 1995). Recently, it has been reported that administration of human chymase induce infiltration of leukocytes including eosinophils in mice as well as guinea pigs (*Br. J. Pharmacol.* 125, 1491, 1998). Further, it has been reported that human chymase acts on the precursor of IL-1β (Interleukin 1β) and converts it to active type IL-1β (*J. Exp. Med.* 174, 821, 1991), which is known to induce eosinophil inflation by augmentation of expression of cell adhesion molecules (*Am. J. Respir. Cell. Mo. Biol.* 13, 555, 1995, *J. Invest. Dermatol.* 100, 417, 1993). Moreover, chymase cleaves membrane-bound stem cell factor (SCF) to form soluble SCF (*Proc. Natl. Acad. Sci. U.S.A.* 94, 9017, 1997). Further, recently, it has been reported that SCF is involved in the accumulation of eosinophils (*J. Immunol.* 156, 3945, 1996). These findings suggest that chymase is related to the role of eosinophils. At the present time, a search is going on for substances which can inhibit the activity of chymase in vivo with the aim of clarifying the role of chymase in the body and the possibility of chymase inhibitors as pharmaceuticals.

There are chymase inhibitors such as low molecular weight chymase inhibitors such as shown in textbooks (*Protease Inhibitors*; Barrett et al., Eds; Elssevier Science B. V.; Amsterdam, 1996), α-keto acid derivatives reported as peptide type inhibitors (WO93-25574, *Proc. Natl. Acad. Sci. USA*, 1995, 92, 6738), α,α-difluoro-β-keto acid derivatives (Japanese Unexamined Patent Publication (Kokai) No. 9-124691), tripeptide inhibitors (WO93-03625), phosphoric acid derivatives (Oleksyszyn et al., *Biochemistry* 30, 485, 1991), peptide like inhibitors such as trifluoromethylketone derivatives (WO96-33974, Japanese Unexamined Patent Publication (Kokai) No. 10-53579) and acetoamide derivatives (Japanese Unexamined Patent--Publication (Kokai) No. 10-7661, Japanese Unexamined Patent Publication (Kokai) No. 10-53579, Japanese Unexamined Patent Publication (Kokai) No. 11-246437, WO99-41277, WO98-18794, WO96-39373), non-peptide type inhibitors such as triazine derivatives (Japanese Unexamined Patent Publication (Kokai) No. 8-208654 and Japanese unexamined Patent Publication (Kokai) No. 10-245384), phenol ester derivatives (Japanese Unexamined Patent Publication (Kokai) No. 10-87567), cephem derivatives (Japanese Unexamined Patent Publication (Kokai) No. 10-87493), isoxazole derivatives (Japanese Unexamined Patent Publication (Kokai) No. 11-1479), imidazolidine derivatives (WO96-04248), hydantoin derivatives (Japanese Unexamined Patent Publication (Kokai) No. 9-31061), quinazoline derivatives (WO97-11941), etc. have been reported, but no satisfactory medicament or treatment method using inhibition of the activity of chymase as a strategy for treatment has yet been established.

DISCLOSURE OF THE INVENTION

The object of the present invention is to provide safe medicament for the prevention or treatment of diseases accompanied with an increase in eosinophils, which suppresses the progress of the condition, prevents progress of complications, and improves the quality of life of the patient.

The present inventors engaged in intensive studies to attain the above object and, as a result, found that a chymase inhibitor specifically reduces the number of eosinophils in the peripheral blood, elucidated the relationship between chymase activity and the increase in number of eosinophils, whereby the present invention is completed.

In accordance with the present invention, there is provided a medicament for the prevention or treatment of diseases involving an increase of eosinophils having a chymase inhibitor as its effective ingredient.

In accordance with the present invention, there is also provided a pharmaceutical composition for the prevention or treatment of allergic diseases containing an amount of a chymase inhibitor suppressing an increase in the eosinophils and a pharmaceutically acceptable vehicle.

In accordance with the present invention, there is further provided a medicament for the suppression of an increase in eosinophils having a chymase inhibitor as its effective ingredient.

BEST MODE FOR CARRYING OUT THE INVENTION

In this specification, the diseases involving an increase in eosinophils include diseases whose onset is caused by an increase of eosinophils, diseases whose conditions are aggravated by an increase in eosinophils, and diseases whose cure is delayed by an increase in eosinophils. These diseases include, for example, allergic diseases such as bronchial asthma, allergic rhinitis, allergic conjunctivitis, cnidosis, and eczema.

The chymase inhibitor able to be used in the present invention can be selected as a substance inhibiting chymase activity by the use of methods workable by persons skilled in the art. As the method of selection, for example, the method of Example 1 explained below may be used. The compounds obtained in this way include known compounds previously reported as chymase inhibitors, for example, the low molecular weight chymase inhibitors such as shown in textbooks (*Protease Inhibitors*; Barrett et al., Eds; Elssevier Science B. V.; Amsterdam, 1996), α-keto acid derivatives reported as peptide type inhibitors (WO93-25574, *Proc. Natl. Acad. Sci. USA*, 1995, 92, 6738), α,α-difluoro-β-keto acid derivatives (Japanese Unexamined Patent Publication (Kokai) No. 9-124691), tripeptide inhibitors (WO93-03625), phosphoric acid derivatives (Oleksyszyn et al., *Biochemistry* 30, 485, 1991), peptide like inhibitors such as trifluoromethylketone derivatives (WO96-33974, Japanese Unexamined Patent Publication (Kokai) No. 10-53579) and acetoamide derivatives (Japanese Unexamined Patent Publication (Kokai) No. 10-7661, Japanese Unexamined Patent Publication (Kokai) No. 10-53579, Japanese Unexamined Patent Publication (Kokai) No. 11-246437, WO99-41277, WO98-18794, WO96-39373), non-peptide type inhibitors such as triazine derivatives (Japanese Unexamined Patent Publication (Kokai) No. 8-208654 and Japanese Unexamined Patent Publication (Kokai) No. 10-245384), phenol ester derivatives (Japanese Unexamined Patent Publication (Kokai) No. 10-87567), cephem derivatives (Japanese Unexamined Patent Publication (Kokai) No. 10-87493), isoxazole derivatives (Japanese Unexamined Patent Publication (Kokai) No. 11-1479), imidazolidine derivatives (WO96-04248), hydantoin derivatives (Japanese Unexamined Patent Publication (Kokai) No. 9-31061), quinazoline derivatives (WO97-11941), etc., but as a representative example of a preferable chymase inhibitor, a compound of the following formula (I) and its pharmaceutically acceptable salts may be mentioned.

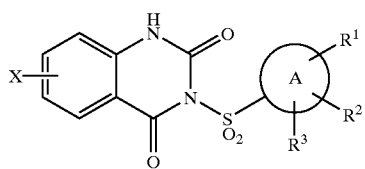

(I)

wherein, the ring A represents an aryl group;

$R^1$ represents a hydroxyl group, an amino group, a $C_1$ to $C_4$ lower alkylamino group which may be substituted with a carboxylic acid group, a $C_7$ to $C_{10}$ lower aralkylamino group which may be substituted with a carboxylic acid group, an amino group acylated with a $C_1$ to $C_4$ lower aliphatic acid which may be substituted with a carboxylic acid group, an amino group acylated with an aromatic ring carboxylic acid which may be substituted with a carboxylic acid group, an amino group acylated with a heteroaromatic ring carboxylic acid which may be substituted with a carboxylic acid group, an amino group sulfonylated with a $C_1$ to $C_4$ lower alkanesulfonic acid which may be substituted with a carboxylic acid group, an amino group sulfonylated with an aromatic ring sulfonic acid which may be substituted with a carboxylic acid group, an amino group sulfonylated with a heteroaromatic ring sulfonic acid which may be substituted with a carboxylic acid group, a $C_1$ to $C_4$ lower alkyl group substituted with a carboxylic acid group, or a $C_2$ to $C_4$ lower alkylene group which may be substituted with a carboxylic acid group;

$R^2$ and $R^3$ may be the same or different and represent a hydrogen atom, an unsubstituted or substituted $C_1$ to $C_4$ lower alkyl group, a halogen atom, a hydroxyl group, a $C_1$ to $C_4$ lower alkoxyl group, an amino group, an unsubstituted or substituted $C_1$ to $C_4$ lower alkylamino group, an unsubstituted or substituted $C_7$ to $C_{10}$ aralkylamino group, an amino group acylated with a $C_1$ to $C_4$ lower aliphatic acid which may be substituted with a carboxylic acid group, an amino group acylated with an aromatic ring carboxylic acid which may be substituted with a carboxylic acid group, an amino group acylated with a heteroaromatic ring carboxylic acid which may be substituted with a carboxylic acid group, an amino group sulfonylated with a $C_1$ to $C_4$ lower alkanesulfonic acid which may be substituted with a carboxylic acid group, an amino group sulfonylated with an aromatic ring sulfonic acid which may be substituted with a carboxylic acid group, an amino group sulfonylated with a heteroaromatic ring sulfonic acid which may be substituted with a carboxylic acid group, or a carboxylic acid group or when the ring A is a benzene ring, $R^1$ and $R^2$ may form, together with the substituting benzene ring, a fused heterocyclic ring which may be substituted with a carboxylic acid and in which the carbon atom in the ring may form a carbonyl group and $R^3$ is the same as defined above; and X represents a hydrogen atom, a $C_1$ to $C_4$ lower alkyl group, a $C_1$ to $C_4$ lower alkoxy group, a halogen atom, a hydroxyl group, an amino group, or a nitro group.

In the general formula (I), preferable examples of the aryl group represented by the ring A are a benzene ring and a naphthalene ring.

Preferable examples of the $C_1$ to $C_4$ lower alkylamino group which may be substituted with the carboxylic acid group and the $C_7$ to $C_{12}$ lower aralkylamino group which may be substituted with a carboxylic acid group represented by $R^1$ are a methylamino group, an ethylamino group, a propylamino group, a butylamino group, a carboxymethylamino group, a carboxyethylamino group, a carboxypropylamino group, a carboxybutylamino group, a benzylamino group, a phenetylamino group, a phenylpropylamino group, a phenylbutylamino group, a carboxybenzylamino group, a carboxyphenetylamino group, a carboxyphenylpropylamino group, a carboxyphenylbutylamino group, etc.

Preferable examples of the amino group acylated with a $C_1$ to $C_4$ lower aliphatic acid which may be substituted with a carboxylic acid group, the amino group acylated with an aromatic ring carboxylic acid which may be substituted with a carboxylic acid group, and the amino group acylated with a heteroaromatic ring carboxylic acid which may be substituted with a carboxylic acid group represented by $R^1$ are a formylamino group, an acetylamino group, a propionylamino group, a butyrylamino group, a benzoylamino group, a naphthoylamino group, a pyridinecarbonylamino group, a pyrrolecarbonylamino group, a carboxyacetylamino group, a carboxypropionylamino group, a carboxybutyrylamino group, a carboxybenzoylamino group, a carboxynaphthoylamino group, a carboxypyridinecarbonylamino group, a carboxypyrrolecarbonylamino group, etc.

Preferable examples of the amino group sulfonylated with a $C_1$ to $C_4$ lower alkanesulfonic acid which may be substituted with a carboxylic acid group, the amino group sulfonylated with an aromatic ring sulfonic acid which may be substituted with a carboxylic acid group, and the amino group sulfonylated with a heteroaromatic ring sulfonic acid which may be substituted with a carboxylic acid group represented by $R^1$ are a methanesulfonylamino group, an ethanesulfonylamino group, a propanesulfonylamino group, a butanesulfonylamino group, a benzenesulfonylamino group, a naphthalenesulfonylamino group, a pyridinesulfonylamino group, a pyrrolesulfonylamino group, a carboxymethanesulfonylamino group, a carboxyethanesulfonylamino group, a carboxypropanesulfonylamino group, a carboxybutanesulfonylamino group, a carboxybenzenesulfonylamino group, a carboxynaphthalenesulfonylamino group, a carboxypyridinesulfonylamino group, a carboxypyrrolesulfonylamino group, etc.

Preferable examples of the $C_1$ to $C_4$ lower alkyl group substituted with a carboxylic acid group represented by $R^1$ are an acetic acid group, a propionic acid group, a butyric acid group, a valeric acid group, etc.

Preferable examples of the $C_2$ to $C_4$ lower alkylene group substituted with a carboxylic acid group represented by $R^1$ are an acrylic acid group, a crotonic acid group, etc.

Preferable examples of the unsubstituted or substituted $C_1$ to $C_4$ lower alkyl group represented by $R^2$ or $R^3$ are a straight-chain alkyl group such as a methyl group, an ethyl group, a n-propyl group, and a n-butyl group and a branched alkyl group such as an isopropyl group, a sec-butyl group, and a t-butyl group.

Preferable examples of the substituent group of the $C_1$ to $C_4$ lower alkyl group are a carboxylic acid group, a halogen atom such as a fluorine atom and a chlorine atom, a $C_1$ to $C_4$ lower alkoxy group, an amino group, a methylamino group, a dimethylamino group, a carboxymethylamino group, a carboxyethylamino group, etc.

Preferable examples of the halogen atom represented by $R^2$ or $R^3$ are a fluorine atom, a chlorine atom, a bromine atom and an iodine atom.

Preferable examples of the $C_1$ to $C_4$ lower alkoxyl group represented by $R^2$ or $R^3$ are a straight-chain alkyloxy group such as a methoxy group, an ethoxy group, a n-propyloxy group, and a n-butoxy group and a branched alkyloxy group such as an isopropyloxy group, a sec-butoxy group, and a t-butoxy group.

Preferable examples of the unsubstituted or substituted $C_1$ to $C_4$ lower alkylamino group represented by $R^2$ or $R^3$ are a methylamino group, an ethylamino group, a propylamino group, a butylamino group, etc.

Preferable examples of the substituent group of the $C_1$ to $C_4$ lower alkylamino group are a carboxylic acid group, a halogen atom such as a fluorine atom and a chlorine atom, a $C_1$ to $C_4$ lower alkoxyl group, etc.

Preferable examples of the unsubstituted or substituted $C_7$ to $C_{12}$ lower aralkylamino group represented by $R^2$ or $R^3$ are a benzylamino group, a phenylethylamino group, a phenylpropylamino group, a phenylbutylamino group, etc.

Preferable examples of the substituent group of the aralkylamino group are a carboxylic acid group, a halogen atom such as a fluorine atom and a chlorine atom, a $C_1$ to $C_4$ lower alkoxyl group, etc.

Preferable examples of the amino group acylated with a $C_1$ to $C_4$ lower aliphatic acid which may be substituted with a carboxylic acid group, the amino group acylated with an aromatic ring carboxylic acid which may be substituted with a carboxylic acid group, and the amino group acylated with a heteroaromatic ring carboxylic acid which may be substituted with a carboxylic acid group represented by $R^2$ or $R^3$ are a formylamino group, an acetylamino group, a propionylamino group, a butyrylamino group, a benzoylamino group, a naphthoylamino group, a pyridinecarbonylamino group, a pyrrolecarbonylamino group, a carboxyacetylamino group, a carboxypropionylamino group, a carboxybutyrylamino group, a carboxybenzoylamino group, a carboxynaphthoylamino group, a carboxypyridinecarbonylamino group, a carboxypyrrolecarbonylamino group, etc.

Preferable examples of the amino group sulfonylated with a $C_1$ to $C_4$ lower alkanesulfonic acid which may be substituted with a carboxylic acid group, the amino group sulfonylated with an aromatic ring sulfonic acid which may be substituted with a carboxylic acid group, and the amino group sulfonylated with a heteroaromatic ring sulfonic acid which may be substituted with a carboxylic acid group represented by $R^2$ or $R^3$ are a methanesulfonylamino group, an ethanesulfonylamino group, a propanesulfonylamino group, a benzenesulfonylamino group, a naphthalenesulfonylamino group, a pyridinesulfonylamino group, a pyrrolesulfonylamino group, a carboxymethanesulfonylamino group, a carboxyethanesulfonylamino group, a carboxypropanesulfonylamino group, a carboxybenzenesulfonylamino group, a carboxynaphthalenesulfonylamino group, a carboxypyridinesulfonylamino group, a carboxypyrrolesulfonylamino group, etc.

Preferable examples of the fused heterocyclic ring which may be substituted with a carboxylic acid and in which the carbon atom in the ring may form a carbonyl group which $R^1$ and $R^2$ form together with the substituting benzene ring when the ring A is a benzene ring, are a tetrahydroquinoline ring and a benzoxazine ring, for example, a tetrahydroquinoline, a benzoxazine, a quinoxaline, a benzodioxane, a carboxytetrahydroquinoline, a carboxybenzoxazine, a carboxyquinoxaline, a carboxybenzodioxane, etc.

Preferable examples of the $C_1$ to $C_4$ lower alkyl group represented by X are a straight-chain alkyl group such as a methyl group, an ethyl group, a n-propyl group, and a n-butyl group and a branched alkyl group such as an isopropyl group, a sec-butyl group, and a t-butyl group.

Preferable examples of the $C_1$ to $C_4$ lower alkoxyl group represented by X are a straight-chain alkyloxy group such as a methoxy group, an ethoxy group, a n-propyloxy group, and a n-butoxy group and a branched alkyloxy group such as an isopropyloxy group, a sec-butoxy group, and a t-butoxy group.

Preferable examples of the halogen atom represented by X, are a fluorine atom, a chlorine atom, a bromine atom and an iodine atom.

Further, examples of a pharmaceutically acceptable salts are an acid salt such as a hydrochloric acid salt, a methanesulfonic acid salt, and a trifluoroacetic acid salt and an alkali metal salt such as a sodium salt and a potassium salt.

The quinazoline derivative having the formula (I) according to the present invention may, for example, be synthesized by the following Synthesis Method (A) or (B).

Synthesis Method (A)

A compound having the formula (I-1):

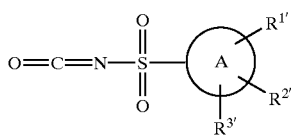
(I-1)

wherein the ring A is the same as defined above and $R^{1'}$, $R^{2'}$ and $R^{3'}$ represent $R^1$, $R^2$ and $R^3$, which may be protected with a protecting group, respectively, and $R^1$, $R^2$ and $R^3$ represent the same as defined above is reacted with an anthranilic acid derivative having the formula (I-2):

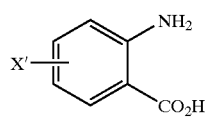
(I-2)

wherein X' represents X, which may be protected with a protecting group, and X represents the same as defined above using the method described, for example, in JP-A-6-199839 to obtain a sulfonylurea derivative having the formula (I-3):

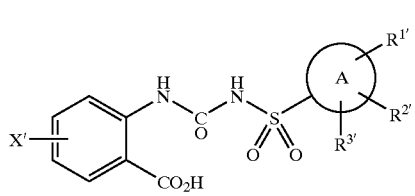
(I-3)

wherein the ring A, $R^{1'}$, $R^2$, $R^{3'}$ and X' represent the same as defined above, then, a condensing agent for example, 1,1'-carbonyldiimidazole (hereinafter referred to as CDI) is used to obtain the quinazoline ring, and if necessary, the protecting groups of $R^1$, $R^2$, $R^3$ and X are deprotected.

In this reaction, when $R^1$, $R^2$ or $R^3$ represents a group containing a hydroxyl group, an amino group, or a carboxylic acid group, $R^1$, $R^2$ or $R^3$ may be optionally protected by a protecting group such as a benzyloxycarbonyl group, a t-butoxycarbonyl group, a benzyl group, an allyl group, a t-butyl group, etc. When X represents a hydroxyl group or an amino group, X may be optionally protected with a protecting group such as a benzyloxycarbonyl group, a t-butoxycarbonyl group, a benzyl group, an allyl group, a t-butyl group, etc.

The compound having the formula (I-1) used in this reaction includes a commercially available or known compound or a compound which can be synthesized by a known method may be used. For example, using the synthesis method described in the specification of European Patent No. 0269141, it is possible to use a compound which can be synthesized from the corresponding sulfonamide derivative using chlorosulfonyl isocyanate. For example, it is possible to use 3-allyloxycarbonylmethylbenzenesulfonyl isocyanate, 4-allyloxycarbonylmethylbenzenesulfonyl isocyanate, 4-allyloxybenzenesulfonyl isocyanate, etc.

As the anthranilic acid derivative having the formula (I-2) used for this reaction, a commercially available or known compound or a compound which can be synthesized by a known method may be used. For example, anthranilic acid, 4-chloroanthranilic acid, 4-methoxyanthranilic acid, 5-chloroanthranilic acid, 4-hydroxyanthranilic acid, etc. may be used.

The reaction to obtain the quinazoline ring from the sulfonylurea derivative having the formula (I-3) may be carried out using an aprotonic solvent such as, for example, an ether solvent such as tetrahydrofuran and dioxane, a halogen-containing solvent such as methylene chloride, or dimethylformamide etc. at a temperature of −50° C. to 50° C., preferably −20° C. to room temperature. Further, for the cyclization reaction, it is possible to use an ordinary condensing agent which includes, for example, CDI, dicyclohexylcarbodiimide (DCC), and similar carbodiimide compounds, mixed anhydrides, etc. The deprotecting reaction can be carried out by an ordinary method using hydrolysis with an acid or alkali, reduction or oxidation etc.

Synthesis Method (B)

A compound having the formula (I-4):

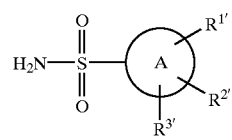
(I-4)

wherein the ring A, $R^{1'}$, $R^{2'}$ and $R^{3'}$ represent the same as defined above is condensed with an anthranilic acid derivative having the formula (I-5):

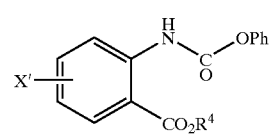
(I-5)

wherein X' represents the same as defined above, Ph represents a phenyl group, and $R^4$ represents a protecting group of the carboxyl group, which is specifically a group capable of being released by hydrolysis or hydrogenolysis, such as, for example, a methyl group, an ethyl group, or a benzyl group using, for example, 1,8-diazabicyclo[5,4,0]-7-undecene (hereinafter referred to as DBU) to form a sulfonylurea derivative having the formula (I-6):

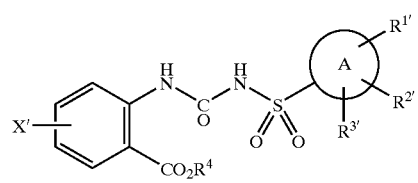
(I-6)

wherein the ring A, $R^{1'}$, $R^{2'}$, $R^{3'}$, $R^4$ and X' are the same as defined above, which is then hydrolyzed with an alkali or hydrogenolyzed to derive a corresponding carboxylic acid represented by the formula (I-3), then the quinazoline ring is obtained and optionally the protecting groups of $R^1$, $R^2$, $R^3$ and X are deprotected, in the same way as in Synthesis Method (A). In this reaction, when $R^1$, $R^2$ or $R^3$ represents a group containing a hydroxyl group, an amino group, or a carboxylic acid group, $R^1$, $R^2$ or $R^3$ may be optionally protected by a protecting group such as a benzyloxycarbonyl group, a t-butoxycarbonyl group, a benzyl group, an allyl group, a t-butyl group, etc. When X represents a hydroxyl group or an amino group, X may be optionally protected with a protecting group such as a benzyloxycarbonyl group, a t-butoxycarbonyl group, a benzyl group, an allyl group, a t-butyl group, etc.

As the compound having the formula (I-4) used in the reaction, a commercially available or known compound or a compound which can be synthesized by a known method may be used. For example, 3-hydroxybenzenesulfonamide, 2-aminobenzenesulfonamide, 3-aminobenzenesulfonamide, 4-aminobenzenesulfonamide, (±)-2-(4-aminosulfonylphenyl)butyric acid, 3-benzyloxycarbonylamino-4-chlorobenzenesulfonamide, 4-benzyloxycarbonylamino-3-chlorobenzenesulfonamide, 4-amino-3,5-dichlorobenzenesulfonamide, 3-benzyloxycarbonylamino-4-methylbenzenesulfonamide, 4-t-butoxycarbonyl-3-hydroxybenzenesulfonamide, 3-benzyloxycarbonylamino-4-t-butoxycarbonylbenzenesulfonamide, 4-t-butoxycarbonyl-3-hydroxybenzenesulfonamide, 3-t-butoxycarbonyl-4-hydroxybenzenesulfonamide, 3-acetamide-4-methoxybenzenesulfonamide, 3-(3-aminosulfonyl)phenylacrylic acid t-butylester, 3-amino-4-methoxybenzenesulfonamide, 4-methoxy-3-methylsulfonylaminobenzenesulfonamide, 3-carboxy-4-hydroxy-2-naphthalenesulfonamide, 4-benzyloxycarbonylamino-3-t-butoxycarbonylbenzenesulfonamide, (±)-3-t-butoxycarbonyl-2-oxo-1H,3H-quinoline-7-sulfonamide, (±)-2-t-butoxycarbonyl-3-oxo-1,4-benzoxazine-6-sulfonamide, etc. may be used.

As the anthranilic acid derivative having the formula (I-5) used in this reaction, a commercially available or known compound or a compound which can be synthesized by a known method may be used. For example, methyl 4-chloro-2-N-phenoxycarbonylanthranilate, ethyl 4-chloro-2-N-phenoxycarbonylanthranilate, benzyl 4-chloro-2-N-phenoxycarbonylanthranilate, methyl 5-chloro-2-N-phenoxycarbonylanthranilate, ethyl 5-chloro-2-N-phenoxycarbonylanthranilate, benzyl 5-chloro-2-N-phenoxycarbonylanthranilate, methyl 4-methoxy-2-N-phenoxycarbonylanthranilate, ethyl 4-methoxy-2-N-phenoxycarbonylanthranilate, benzyl 4-methoxy-2-N-phenoxycarbonylanthranilate, methyl 4-hydroxy-2-N-phenoxycarbonylanthranilate, ethyl 4-hydroxy-2-N-phenoxycarbonylanthranilate, benzyl 4-hydroxy-2-N-phenoxycarbonylanthranilate, etc. may be used.

The reaction for obtaining the compound having the formula (I-4) and the anthranilic acid derivative having the formula (I-5) condense to obtain a sulfonylurea derivative having the formula (I-6), may be carried out using an aprotic solvent, for example, an ether solvent such as tetrahydrofuran or dioxane, a halogen-containing solvent such as methylene chloride, or dimethylformamide etc. at a temperature of −50° C. to 50° C. preferably −20° C. to room temperature. Further, as the usable for the condensation reaction, an organic strong base such as DBU, inorganic bases such as potassium carbonate, sodium carbonate, potassium hydroxide, and sodium hydroxide, or metal bases such as sodium hydride may be used.

In the reaction for alkali hydrolysis or hydrogenolysis of the sulfonylurea derivative having the formula (1-6) thus obtained to obtain the sulfonylurea derivative having the formula (I-3), ordinary hydrolysis conditions or hydrogenolysis conditions for esters may be used.

Note that the above reaction may be carried out while protecting the functional groups not involved in the reaction. According to the type of the protecting group, the protection is removed by chemical reduction or other ordinary protection-removing reactions. For example, when the protecting group is a t-butyl group or t-butoxycarbonyl group, trifluoroacetic acid may be used, while when it is an allyl group, palladium catalysts such as tetrakis(triphenylphosphine)palladium (0) may be used.

The compound having the formula (I), wherein $R^1$ represents an amino group acylated with a $C_1$ to $C_4$ lower aliphatic acid which may be substituted with a carboxylic acid, an amino group acylated with an aromatic ring carboxylic acid which may be substituted with a carboxylic acid and an amino group acylated with an heteroaromatic ring carboxylic acid which may be substituted with a carboxylic acid, can be obtained from the compound having the formula (I), wherein $R^1$ represents an amino group, by acylating the same with carboxylic acid, carboxylic acid chloride, carboxylic acid anhydride using an ordinary method.

The compound having the formula (I), wherein $R^1$ represents an amino group sulfonylated with a $C_1$ to $C_4$ lower alkane sulfonic acid which may be substituted with a carboxylic acid, an amino group sulfonylated with an aromatic ring sulfonic acid which may be substituted with a carboxylic acid and an amino group sulfonylated with an heteroaromatic ring sulfonic acid which may be substituted with a carboxylic acid, can be obtained from the compound having the formula (I), wherein $R^1$ represents an amino group, by sulfonylating the same with sulfonic acid or sulfonic acid chloride using an ordinary method.

The product obtained according to the above-mentioned processes can be purified by a method such as recrystallization or column chromatography.

If necessary, the compounds having the formula (I) of the present invention obtained according to the above-mentioned processes can each be reacted with one of various acids or basis to convert the compound into their salt. Exemplary acids usable for the conversion of the compound having the formula (I) into their salts can include inorganic acids such as hydrochloric acid, hydrobromic acid, nitric acid, sulfuric acid, phosphoric acid; and organic acids such as methanesulfonic acid, benzenesulfonic acid, p-toluenesulfonic acid, trifluoroacetic acid, citric acid, lactic acid, maleic acid, fumaric acid, tartaric acid, acetic acid, adipic acid, palmitic acid and tannic acid. Exemplary usable basis for the conversion of the compound having the formula (I) into their salts can include sodium hydroxide, lithium hydroxide and potassium hydroxide.

Further, the compounds having the formula (I) according to the present invention include those containing asymmetric centers. Each racemic mixture can be isolated by one or more of various methods, whereby a single optically-active substance can be obtained. Usable methods include, for example:

(1) Isolation by optically active column.
(2) Isolation by recrystallization subsequent to conversion into a salt with an optically active acid or base.
(3) Isolation by a combination of the above methods (1) and (2).

Evaluation of a medicament for the prevention or treatment for the disease related to eosinophil increase (e.g., bronchial asthma, allergic rhinitis, allergic conjunctivitis, cnidosis, eczema) can be performed by using peripheral eosinophilia models in addition to use of various disease models. For example, it is known that the number of peripheral eosinophils dramatically increases in the patients with asthma (in particular, chronic asthma) (*Br. Med. J.* 285 (6350), 1229, 1982), but administration of a steroid effective against bronchial asthma reduces the number of eosinophils in the peripheral blood (*Eur. Respir. J. Suppl.* 430s, 1989). It has been known for a long time that parasites such as *Nippostrongylus brasiliensis* cause an increase in eosinophils in animals. (*Proc. Natl. Acad. Sci. USA* 85, 4460, 1988). There has actually been a report that a steroid effective against bronchial asthma suppresses the increase in eosinophils induced by *Nippostrongylus brasiliensis* (*Lab. Invest.* 64, 224, 1991). Thus, parasite-induced eosinophilia model is thought to be useful for evaluation of a medicament for the prevention or treatment for asthma in which eosinophils play an important role. Such a parasite-induced model can also be used for evaluating amendicament for the prevention or treatment for other diseases in which eosinophils are involved e.g., allergic rhinitis, allergic conjunctivitis, cnidosis, and eczema.

The compound of the present invention can be evaluated by the suppressing effect on increase in eosinophils using the method described in Example 2, which is parasite-induced eosinophilia model.

To use the effective ingredient of the present invention as a pharmaceutical composition for the prevention or treatment of eosinophilia, various allergic diseases, and other diseases in which eosinophilis are involved, one or more of the compounds of the present invention may be mixed and formed into a form suitable for use in the method of administration by an ordinary method. Examples of preparation forms for oral administration include capsules, tablets, granules, fine granules, syrups, dry syrups, and other preparations, while examples of preparation forms for non-oral administration include injections and besides suppositories such as rectal suppositories and vaginal suppositories, transnasal preparations such as sprays and ointments, and percutaneous preparations such as tapes for percutaneous absorption.

The clinical dose of the compound according to the present invention varies according to the diseased condition, degree of seriousness, age, presence of complications, etc. and also varies according to its preparation form. In the case of oral administration, however, it may be dosed usually, in terms of effective ingredients, as 1 to 1000 mg per adult per day. In the case of non-oral administration, it is sufficient to administer ¹⁄₁₀ to ½ the amount of the case of oral administration. These dosages can be suitably adjusted according to the age, the diseased condition, and the like of the patient to be dosed.

In the present invention, the chymase inhibitor can be administered alone as it is without being mixed with another effective ingredient, but considering the disease in question, the symptoms, complications, etc., it may also administered as a medicinal preparation containing other effective ingredients. Further, it may also be combined with these other effective ingredients. The amounts of the other effective ingredients used are not particularly limited, but are determined considering the minimum amounts for expression of their effects alone, the occurrence of side effects, etc.

In treatment, the form of preparation and the method of combined treatment including preparations containing the chymase inhibitor alone as an effective ingredient and preparations also containing other effective ingredients are suitably selected by a physician in accordance with the age of the patient, the symptoms, etc.

The toxicity of the compound according to the present invention is low. The acute toxicity values $LD_{50}$ at 24 hours after oral administration to 5-week old male mice were 1 g/kg or more. This value is 50 or more times of the expected clinical amount of use and therefore these compounds are considered to be highly safe.

EXAMPLES

The present invention will now be further explained by, but is by no means limited to, the following Examples, but the scope of the invention is not limited to these Examples needless to say.

Preparation Example 1

Synthesis of 7-chloro-3-(3-hydroxybenzenesulfonyl)-2,4(1H,3H)-guinazolinedione (Compound 1)

Following the Synthesis Method (B), 938 mg (5.42 mmol) of 3-hydroxybenzenesulfonamide was dissolved in 40 ml of tetrahydrofuran, then 892 μl (5.96 mmol) of 1,8-diazabicyclo[5,4,0]-7-undecene (hereinafter referred to as DBU) was added dropwise. The reaction solution was stirred at room temperature for 15 minutes, then 1.66 g (5.42 mmol) of methyl 4-chloro-2-N-phenoxycarbonylanthranilate was added and the mixture was stirred at room temperature overnight. An excess amount of water was poured into the reaction solution, then the mixture was made acidic with hydrochloric acid and extracted with ethyl acetate. The organic layer was washed with water and saturated saline, dried over anhydrous magnesium sulfate, and concentrated. The crude product thus obtained was purified by silica gel column chromatography (0% to 5% methanol/dichloromethane) to obtain 1.23 g (yield 59%) of methyl 4-chloro-2-{[(3-hydroxybenzenesulfonylamino)carbonyl]amino}benzoate. Properties: colorless amorphous, PMR (δ ppm, DMSO-$d_6$): 3.91 (3H, s), 7.02 (1H, m), 7.09 (1H, m), 7.34 (1H, t), 7.57 (2H, m), 7.89 (1H, d), 8.38 (1H, d), 10.94 (1H, s). Next, the 1.23 g (3.2 mmol) of the compound thus obtained was dissolved in 20 ml of methanol, then 10 ml of 2N sodium hydroxide aqueous solution was added dropwise. The reaction solution was stirred at room temperature for 15 minutes, then an excess amount of water was added and the mixture was made acidic with hydrochloric acid. This was then stirred to cause crystals to precipitate which were then obtained by filtration and dried to obtain carboxylic acid. The product thus obtained was dissolved in 50 ml of tetrahydrofuran (hereinafter referred to as THF), then 434 mg (2.68 mmol) of CDI was added under ice cooling and the mixture was stirred for 30 minutes. The reaction solution was diluted with ethyl acetate, washed with water and saturated saline, and dried over anhydrous magnesium sulfate, then concentrated to obtain a crude product. The crude product was purified by silica gel column chromatography (ethyl acetate:n-hexane=1:2) to obtain 230 mg (yield 20%: 2 steps) of the above-identified compound. Properties: colorless crystal, Melting point: >200° C. (decomposition), PMR (δ ppm, DMSO-$d_6$): 7.12 (2H, s), 7.24 (1H, d), 7.48 (1H, t), 7.58 (2H, s), 7.85 (1H, d), 10.28 (1H, s), 11.63 (1H, s).

Preparation Example 2

Synthesis of 3-(2-aminobenzenesulfonyl)-7-chloro-2,4(1H,3H)-quinazolinedione (Compound 2)

2.7 g (15.7 mmol) of 2-aminobenzenesulfonamide and 4.8 g (15.7 mmol) of methyl 4-chloro-2-N- phenoxycarbonylanthranilate were treated in the same way as Preparation Example 1 to obtain 3.2 g (yield 58%: 3 steps) of the above-identified compound. Properties: colorless crystal, Melting point: >200° C. (decomposition), PMR (δ ppm, DMSO-d$_6$): 6.46 (2H, s), 6.65 (1H, t), 6.81 (1H, d), 7.12 (1H, s), 7.23 (1H, d), 7.34 (1H, t), 7.76 (1H, d), 7.86 (1H, d).

Preparation Example 3

Synthesis of 7-chloro-3-(2-methylsulfonylaminobenzenesulfonyl)-2,4(1H,3H-quinazolinedione (Compound 3)

22 mg (0.06 mmol) of Compound 2 was dissolved in 200 μl of pyridine, 11.6 μl (0.15 mmol) of methanesulfonyl chloride was added dropwise, then the resultant mixture was stirred at room temperature overnight. An excess amount of water was added to the reaction solution and the mixture was extracted with ethyl acetate. The organic layer was washed with 1N aqueous hydrochloric acid solution and saturated saline, then dried over anhydrous magnesium sulfate and concentrated to obtain a crude product. The crude product was crystallized from diethyl ether to obtain 16 mg (0.04 mmol) of the above-identified compound. Properties: colorless crystal, Melting point: >200° C. (decomposition), PMR (δ ppm, DMSO-d$_6$): 3.61 (3H, s), 7.10 (1H, d), 7.20 (1H, d), 7.74 (1H, d), 7.82–7.90 (4H, m), 8.34 (1H, d), 11.70 (1H, s).

Preparation Example 4

Synthesis of 3-(4-aminobenzenesulfonyl)-7-chloro-2.4(1H.3H)-quinazolinedione (Compound 4)

2.7 g (15.7 mmol) of 4-aminobenzenesulfonamide and 4.8 g (15.7 mmol) of methyl 4-chloro-2-N-phenoxycarbonylanthranilate were treated in the same way as Preparation Example 1 to obtain 7.9 g (yield 94%) of methyl 2-{[(4-aminobenzenesulfonylamino)carbonyl]amino}-4-chlorobenzoate. Properties: colorless amorphous, PMR (δ ppm, DMSO-d$_6$): 3.59 (3H, s), 5.37 (2H, s), 6.45 (2H, d), 6.83 (1H, dd), 7.41 (2H, d), 7.81 (1H, d), 8.66 (1H, d), 9.64 (1H, s).

Then, from the resultant 7.9 g (14.8 mmol) of sulfonylurea product, in the same way, 4.3 g (yield 83%: 2 steps) of the above-identified compound was obtained. Properties: colorless crystal, Melting point: >200° C. (decomposition), PMR (δ ppm, DMSO-d$_6$): 6.39 (2H, s), 6.63 (2H, d), 7.09 (1H, s), 7.22 (1H, d), 7.76 (2H, d), 7.83 (1H, d), 11.51 (1H, s).

Preparation Example 5

Synthesis of 3-(3-carboxymethyl-benzenesulfonyl)-7-chloro-2,4(1H,3H)-quinazolinedione (Compound 5)

Following the Synthesis Method (A), 3.27 g (11.6 mmol) of 3-allyloxycarbonylmethylbenzenesulfonyl isocyanate was dissolved in 100 ml of anhydrous THF, then 1.98 g (11.5 mmol) of 4-chloroanthranilic acid was added and the mixture was stirred at room temperature for 2 hours. The reaction solution was cooled with ice water, then 1.87 g (11.5 mmol) of CDI was added and the resultant mixture was stirred under ice cooling for 30 minutes. An excess amount of water was poured into the reaction solution, then the mixture was extracted with ethyl acetate. The organic layer was washed, dried, and concentrated to obtain a crude product. This was crystallized with a small amount of ethyl acetate to obtain 2.0 g (yield 40%) of 3-(3-allyloxycarbonylmethylbenzenesulfonyl)-7-chloro-2,4(1H,3H)-quinazolinedione. The allyl product thus obtained was dissolved in 100 ml of a formic acid-THF (1:9) mixture and 700 mg of triphenylphosphine was added. The reactor was shaded from light and under nitrogen atmosphere, then 700 mg of tetrakis(triphenylphosphine)palladium (0) was added and the resultant mixture was stirred while shaded at room temperature overnight. The reaction solution was concentrated in vacuo and the solid obtained was washed with methylene chloride to obtain 1.47 g (yield 81%) of the above-identified compound. Properties: colorless crystal, Melting point: >200° C. (decomposition), PMR (δ ppm, DMSO-d$_6$): 3.76 (2H, s), 7.13 (1H, s), 7.24 (1H, d), 7.61–7.69 (2H, m), 7.86 (1H, d), 8.05 (2H, s), 12.50 (1H, br).

Preparation Example 6

Synthesis of 3-(4-carboxymethyl-benzenesulfonyl)-7-chloro-2,4(1H,3H)-quinazolinedione (Compound 6)

1.10 g (3.95 mmol) of 4-allyloxycarbonylmethyl-benzenesulfonyl isocyanate and 678 mg (3.95 mmol) of 4-chloroanthranilic acid were treated in the same way as in Preparation Example 5 to obtain 657 mg (yield 38%) of 3-(4-allyloxycarbonylbenzenesulfonyl)-7-chloro-2,4(1H,3H)-quinazolinedione. 538 mg (1.24 mmol) thereof was treated in the same way to obtain 342 mg of the above-identified compound (yield 70%). Properties: colorless crystal, Melting point: >200° C. (decomposition), PMR (δ ppm, DMSO-d$_6$): 3.75 (2H, s), 7.13 (1H, s), 7.23 (1H, d), 7.61–7.69 (2H, m), 7.86 (1H, d), 8.05 (2H, s), 12.07 (2H, br).

Preparation Example 7

Synthesis of (±-2-{4-[(7-chloro-2,4(1H,3H)-quinazolin-3-yl)sulfonyl]Rhenyl}butyric acid (Compound 7)

1.02 g (3.41 mmol) of t-butyl (±)-2-(4-aminosulfonylphenyl)butyrate acid and 1.04 g (3.41 mmol) of methyl 4-chloro-2-N-phenoxycarbonylanthranilate were treated in the same way as Preparation Example 1 to obtain 1.46 g (yield 84%) of methyl 2-[({4-[1-(t-butoxycarbonyl)propyl]benzenesulfonylamino}carbonyl)amino]-4-chlorobenzoate. Properties: colorless amorphous, PMR (δ ppm, CDC1$_3$): 0.89 (3H, t), 1.38 (9H, s), 1.69–1.76 (1H, m), 2.03–2.10 (1H, m), 3.42 (1H, t), 3.94 (3H, s), 7.04 (1H, d), 7.47 (2H, d), 7.93 (1H, d), 8.01 (2H, d), 8.45 (1H, br), 11.04 (1H, br).

Next, 4.3 ml (8.6 mmol) of 2N sodium hydroxide aqueous solution was used to similarly form carboxylic acid in an amount of 1.43 g and 463 mg (2.86 mmol) of CDI was used to obtain 970 mg (yield 71%: 2 steps) of t-butyl (±)-2-{4-[(7-chloro-2,4(1H,3H)-quinazolin-3-yl)sulfonyl]phenyl}butyrate.

Further, the t-butylester thus obtained was dissolved in 5 ml of dichloromethane, then 5 ml of trifluoroacetic acid was added and the resultant mixture was stirred at room temperature for 40 minutes. The reaction solution was concentrated in vacuo and the resultant crude product was washed with a small amount of diethyl ether to obtain 820 mg-of the above-identified compound (yield 96%). Properties: colorless crystal, Melting point: >200° C. (decomposition), PMR (δ ppm, DMSO-d$_6$): 0.84 (3H, t), 1.67–1.75 (1H, m), 1.98–2.05 (1H, m), 3.62 (1H, t), 7.11 (1H, s), 7.24 (1H, d), 7.61 (2H, d), 7.86 (1H, d), 8.13 (2H, d), 11.62 (1H, s).

Preparation Example 8

Synthesis of 3-(3-amino-4-chlorobenzenesulfonyl)-7-chloro-2,4(1H,3H)-guinazolinedione (Compound 8)

1.0 g (2.93 mmol) of 3-benzyloxycarbonylamino-4-chlorobenzenesulfonamide and 1.18 g (2.93 mmol) of benzyl 4-chloro-2-N-phenoxycarbonylanthranilate were treated in the same way as Preparation Example 1 to obtain 1.43 g (yield 78%) of benzyl 2-{[(3-benzyloxycarbonylamino-4-chlorobenzene sulfonylamino)carbonyl]amino}-4-chlorobenzoate. Properties: colorless amorphous, PMR (δ ppm, DMSO-$d_6$): 5.19 (2H, s), 5.36 (2H, s), 7.21 (1H, dd), 7.34–7.48 (10H, m), 7.72–7.76 (2H, m), 7.97 (1H, d), 8.25 (1H, d), 8.30 (1H, d), 9.53 (1H, s), 10.30 (1H, s). 1.38 g (2.20 mmol) thereof was dissolved in 50 ml of THF, then 200 mg of palladium-carbon (10%) was added and the mixture was stirred under a hydrogen flow for 2 hours. The reaction mixture was filtered with Celite to remove the palladium-carbon, then the filtrate was concentrated in vacuo to obtain a carboxylic acid. The product obtained was suspended in 50 ml of THF, then 356 mg (2.20 mmol) of CDI was added under ice cooling and the resultant mixture was treated in the same way as Preparation Example 1 to obtain 560 mg (yield 66%: 2 steps) of the above-identified compound. Properties: colorless crystal, Melting point: >200° C. (decomposition), PMR (δ ppm, DMSO-$d_6$): 6.00 (2H, s), 7.12 (1H, s), 7.26 (2H, t), 7.48 (1H, d), 7.66 (1H, s), 7.86 (1H, d), 11.76 (1H, br).

Preparation Example 9

Synthesis of 3-(4-amino-3,5-dichlorobenzenesulfonyl)-7-chloro-2,4(1H,3H)-quinazolinedione (Compound 9)

1.06 g (4.40 mmol) of 4-amino-3,5-dichlorobenzenesulfonamide and 1.34 g (4.40 mmol) of methyl 4-chloro-2-N-phenoxycarbonylanthranilate were treated in the same way as Preparation Example 1 to obtain 905 mg (yield 44%) of methyl 2-{([(4-amino-3,5-dichlorobenzenesulfonylamino)carbonyl]amino}-4-chlorobenzoate. Properties: colorless amorphous, PMR (δ ppm, DMSO-$d_6$): 3.87 (3H, s), 6.59 (2H, br), 7.22 (1H, dd), 7.72 (2H, s), 7.93 (1H, d), 8.24 (1H, d), 10.17 (1H, s).

Then, from 905 mg (2.0 mmol) of the resultant sulfonylurea product, in the same way, 660 mg (yield 82%: 2 steps) of the above-identified compound was obtained. Properties: colorless crystal, Melting point: >200° C. (decomposition), PMR (δ ppm, DMSO-$d_6$): 6.80 (2H, s), 7.12 (1H, s), 7.24 (1H, d), 7.86 (1H, d), 7.92 (2H, s), 11.63 (1H, br).

Preparation Example 10

Synthesis of 3-(3-amino-4-methylbenzenesulfonyl)-7-chloro-2,4(in 3H)-quinazolinedione (Compound 10)

960 mg (3.00 mmol) of 3-benzyloxycarbonylamino-4-methylbenzenesulfonamide and 1.14 g (3.00 mmol) of benzyl 4-chloro-2-N-phenoxycarbonylanthranilate were treated in the same way as in Preparation Example 8 to obtain 1.14 g (yield 62% of benzyl 2-{[(3-benzyloxycarbonylamino-4-methylbenzenesulfonylamino)carbonyl]amino}-4-chlorobenzoate. Properties: colorless amorphous, PMR (δ ppm, DMSO-$d_6$): 2.30 (3H, s), 5.17 (2H, s), 5.36 (2H, s), 7.20 (1H, dd), 7.33–7.48 (11H, m), 7.63 (1H, d), 7.97 (1H, d), 8.11 (1H, s), 8.25 (1H, s), 9.27 (1H, s), 10.30 (1H, s), 12.20 (1H, br).

Then, from 1.14 g (1.87 mmol) of the resultant sulfonylurea product, in the same way, 190 mg (yield 27%: 2 steps) of the above-identified compound was obtained. Properties: colorless crystal, Melting point: >200° C. (decomposition), PMR (δ ppm, DMSO-$d_6$): 2.12 (3H, s), 5.47 (2H, s), 7.12 (1H, s), 7.16–7.25 (3H, m), 7.38 (1H, s), 7.85 (1H, d), 11.58 (1H, s).

Preparation Example 11

Synthesis of 3-[(3-carboxymethylaminophenyl)sulfonyl]-7-chloro-2,4(1H.3H)-quinazolinedione (Compound 11)

1.62 g (5.65 mmol) of 3-t-butoxycarbonyl-methylaminobenzenesulfonamide and 1.73 g (5.65 mmol) of methyl 4-chloro-2-N-phenoxycarbonylanthranilate were treated in the same way as in Preparation Example 7 to obtain 209 mg (yield 9%: 4 steps) of the above-identified compound. Properties: colorless crystal, Melting point: >200° C. (decomposition), PMR (δ ppm, DMSO-$d_6$): 3.86 (2H, s), 6.88 (1H, s), 7.12 (1H, s), 7.24 (1H, d), 7.30–7.38 (3H, m), 7.86 (1H, d), 11.61 (1H, br).

Preparation Example 12

Synthesis of 3-(3-aminobenzenesulfonyl)-7-chloro-2,4(1H,3H)-quinazolinedione (Compound 12)

3.5 g (12.9 mmol) of 3-t-butoxycarbonylamino-benzenesulfonamide and 3.9 g (12.8 mmol) of methyl 4-chloro-2-N-phenoxycarbonylanthranilate were treated in the same way as in Preparation Example 7 to obtain 2.2 g (yield 49%: 4 steps) of the above-identified compound. Properties: colorless crystal, Melting point: >200° C. (decomposition), PMR (δ ppm, DMSO-$d_6$): 5.72 (2H, s), 6.87 (1H, d), 7.12 (1H, s), 7.23–7.27 (2H, m), 7.33 (1H, s), 7.86 (1H, d), 11.61 (1H, s).

Preparation Example 13

Synthesis of 2-{3-[(7-chloro-2,4(1H,3H)-quinazolinedion-3-yl)sulfonyl]phenylaminocarbonyl}propionic acid (Compound 13)

100 mg (0.28 mmol) of Compound 12 was dissolved in 5 ml of THF, 100 mg (1.0 mmol) of succinic anhydride was added, and the resultant mixture was heated and refluxed for 3 hours. The reaction solution was concentrated in vacuo and the crude product thus obtained was crystallized with ethyl acetate-diethyl ether to obtain 120 mg (yield 96%) of the above-identified compound. Properties: colorless crystal, Melting point: 187–188° C., PMR (δ ppm, DMSO-$d_6$): 2.54 (2H, d), 2.59 (2H, d), 7.12 (1H, s), 7.24 (1H, d), 7.59 (1H, t), 7.80 (1H, d), 7.86 (1H, d), 7.96 (1H, d), 8.41 (1H, s), 10.40 (1H, s), 11.63 (1H, br), 12.10 (1H, br).

Preparation Example 14

Synthesis of 3-{3-[(7-chloro-2,4(1H,3H)-guinazolinedion-3-yl)sulfonyl]phenyl}acrylic acid (Compound 14)

1.54 g (5.44 mmol) of t-butyl 3-(3-aminosulfonyl)phenylacrylate and 1.66 g (5.44 mmol) of methyl 4-chloro-2-N-phenoxycarbonylanthranilate were treated in the same way as in Preparation Example 7 to obtain 2.18 g (yield 81%) of methyl 2-({[3-(3-t-butoxy-3-oxo-1-propenyl)benzenesulfonylamino]carbonyl}amino)-4-chlorobenzoate.

Properties: colorless amorphous, PMR (δ ppm, CDCl$_3$): 1.53 (9H, s), 3.95 (3H, s), 6.46 (1H, d), 7.05 (1H, d), 7.55 (1H, m), 7.57 (1H, d), 7.72 (1H, m), 7.93 (1H, m), 8.04 (1H, m), 8.27 (1H, s), 8.46 (1H, d), 11.05 (1H, br).

Then, from 2.18 g (4.4 mmol) of the resultant sulfonylurea product, in the same way, 698 mg (yield 37%: 3 steps) of the above-identified compound was obtained. Properties: colorless crystal, Melting point: >200° C. (decomposition), PMR (δ ppm, DMSO-d$_6$): 6.65 (1H, d), 7.12 (1H, s), 7.25 (1H, d), 7.69 (1H, d), 7.72 (1H, t), 7.87 (1H, d), 8.12 (2H, q), 8.37 (1H, s), 11.64 (1H, s).

Preparation Example 15

Synthesis of 4-[(7-chloro-2,4(1H,3H)-guinazolinedion-3-yl)sulfonyl]salicylic acid (Compound 15)

1.0 g (3.66 mmol) of 4-t-butoxycarbonyl-3-hydroxybenzenesulfonamide and 1.12 g (3.66 mmol) of methyl 4-chloro-2-N-phenoxycarbonylanthranilate were treated in the same way as in Preparation Example 7 to obtain 1.79 g (yield 100%) of methyl 2-{[(4-t-butoxycarbonyl-3-hydroxybenzenesulfonylamino)carbonyl]amino}-4-chlorobenzoate. Properties: colorless amorphous, PMR (δ ppm, DMSO-d$_6$): 1.57 (9H, s), 3.87 (3H, s), 7.14 (1H, d), 7.40–7.45 (2H, m), 7.85 (1H, d), 7.92 (1H, d), 8.32 (1H, d), 10.13 (1H, s), 10.82 (1H, s).

Then, from 1.78 g (3.66 mmol) of the resultant sulfonylurea product, in the same way, 370 mg (yield 25%: 3 steps) of the above-identified compound was obtained. Properties: colorless crystal, Melting point: >200° C. (decomposition), PMR (δ ppm, DMSO-d$_6$): 7.13 (1H, s), 7.26 (1H, d), 7.69 (1H, d), 7.87 (1H, d), 8.01 (1H, d), 11.67 (1H, s).

Preparation Example 16

Synthesis of 4-[(7-chloro-2,4(1H,3H)-quinazolinedion-3-yl)sulfonyl]salicylic acid monosodium salt (Compound 16)

50 mg (0.13 mmol) of Compound 15 was suspended in approximately 1 ml of THF, then 126 μl of 1N sodium hydroxide aqueous solution was added dropwise. The solution was confirmed to have become uniform, then 30 ml of water was added and the mixture freeze-dried to quantitatively obtain the above-identified compound in an amorphous state in an amount of 52 mg. Properties: colorless amorphous, PMR (δ ppm, CD$_3$OD): 7.11 (1H, s), 7.19 (1H, d), 7.58 (1H, d), 7.63 (1H, s), 7.92 (1H, d), 8.03 (1H, d).

Preparation Example 17

Synthesis of 4-[(7-chloro-2,4(1H,3H)-guinazolinedion-3-yl)sulfonyl]anthranilic acid (Compound 17)

2.84 g (6.99 mmol) of 3-benzyloxycarbonylamino-4-t-butoxycarbonylbenzenesulfonamide and 2.67 g (6.99 mmol) of benzyl 4-chloro-2-N-phenoxycarbonylanthranilate were treated in the same way as in Preparation Example 8 to obtain 3.74 g (yield 77%) of benzyl 2-{[(3-benzyloxycarbonylamino-4-t-butoxycarbonylbenzenesulfonylamino)carbonyl]amino}-4-chlorobenzoate. Properties: colorless amorphous, PMR (δ ppm, DMSO-d$_6$): 1.54 (9H, s), 5.19 (2H, s), 5.34 (2H, s), 7.05 (1H, m), 7.34–7.58 (10H, m), 7.60 (1H, d), 7.90 (1H, d), 7.98 (1H, d), 8.50 (1H, br), 8.62 (1H, s), 10.00 (,1H, br), 10.41 (1H, s).

Then, from 3.74 g (5.39 mmol) of the resultant sulfonylurea, in the same way, 690 mg (yield 30%: 2 steps) of t-butyl 4-[(7-chloro-2,4(1H,3H)-quinazolinedion-3-yl)sulfonyl]anthranilate was obtained, then this was subjected to a similar debutylation reaction to obtain 503 mg (yield 84%) of the above-identified compound. Properties: colorless crystal, Melting point: >200° C. (decomposition), PMR (δ ppm, DMSO-d$_6$): 7.14 (1H, s), 7.18 (1H, d), 7.25 (1H, d), 7.59 (1H, s), 7.87 (1H, d), 7.89 (1H, d), 11.62 (1H, s).

Preparation Example 18

Synthesis of 4-[(7-chloro-2,4(1H,3H)-quinazolinedion-3-yl)sulfonyl]anthranilic acid monosodium salt (Compound 18)

50 mg (0.13 mmol) of Compound 17 was suspended in approximately 1 ml of THF, then 126 μl of 1N sodium hydroxide aqueous solution was added dropwise. The solution was confirmed to have become uniform, then 30 ml of water was added and the mixture was freeze-dried to quantitatively obtain the above-identified compound in an amorphous state in an amount of 52 mg. Properties: colorless amorphous, PMR (δ ppm, DMSO-d$_6$): 7.11–7.22 (3H, m), 7.37 (1H, s), 7.83 (1H, d), 7.91 (1H, d).

Preparation Example 19

Synthesis of 3-(4-hydroxybenzenesulfonyl)-7-chloro-2,4(1H,3H)-quinazolinedione (Compound 19)

1.50 g (7.03 mmol) of 4-allyloxybenzenesulfonyl isocyanate and 1.2 g (7.03 mmol) of 4-chloroanthranilic acid were treated in the same way as in Preparation Example 5 to obtain 1.5 g (yield 53%) of 3-(4-allyloxybenzenesulfonyl)-7-chloro-2,4(1H,3H)-quinazolinedione. 500 mg (1.27 mmol) thereof was similarly treated to obtain 405 mg of the above-identified compound (yield 90%). Properties: colorless crystal, Melting point: >200° C. (decomposition), PMR (δ ppm, DMSO-d$_6$): 6.98 (2H, d), 7.11 (1H, s), 7.23 (1H, d), 7.85 (1H, d), 8.00 (2H, d), 11.25 (1H, br).

Preparation Example 20

Synthesis of 4-[(2,4(1H,3H)-quinazolinedion-3-yl)sulfonyl]salicylic acid (Compound 20)

618 mg (2.26 mmol) of 4-t-butoxycarbonyl-3-hydroxybenzenesulfonamide and 613 mg (2.26 mmol) of methyl 2-N-phenoxycarbonylanthranilate were treated in the same way as in Preparation Example 17 to obtain 792 mg (yield 78%) of methyl 2-{[(4-t-butoxycarbonyl-3-hydroxybenzene-sulfonylamino)carbonyl]amino}benzoate. Properties: colorless amorphous, PMR (δ ppm, CDCl$_3$): 1.60 (9H, s), 3.97 (3H, s), 7.09 (1H, t), 7.49–7.52 (2H, m), 7.65 (1H, d), 7.90 (1H, d), 8.01 (1H, dd), 8.33 (1H, d), 10.98 (1H, s), 11.18 (1H, s).

Then, from 790 mg (1.75 mmol) of the resultant sulfonylurea product, in the same way, 100 mg (yield 8%: 3 steps) of the above-identified compound was obtained. Properties: colorless crystal, Melting point: >200° C. (decomposition), PMR (δ ppm, DMSO-d$_6$): 7.13 (1H, d), 7.22 (1H, t), 7.63–7.69 (3H, m), 7.87 (1H, d), 8.01 (1H, d), 11.57 (1H, s).

Preparation Example 21

Synthesis of 5-[(7-chloro-2,4(1H,3H)-guinazolinedion-3-yl)sulfonyl]salicylic acid (Compound 21)

320 mg (1.17 mmol) of 3-t-butoxycarbonyl-4-hydroxybenzenesulfonamide and 447 mg (1.17 mmol) of benzyl 4-chloro-2-N-phenoxycarbonylanthranilate were treated in the same way as in Preparation Example 17 to obtain 611 mg (yield 93%) of benzyl 2-{[(3-t-butoxycarbonyl-4-hydroxybenzenesulfonylamino)carbonyl]amino}-4-chlorobenzoate. Properties: colorless amorphous, PMR (δ ppm, CDC$_{13}$): 1.62 (9H, s), 5.35 (2H, s), 7.01–7.05 (2H, m), 7.37–7.41 (5H, m), 7.96 (1H, d), 8.10 (1H, dd), 8.46–8.48 (2H, m), 10.99 (1H, s), 11.66 (1H, s).

Then, from 611 mg (1.09 mmol) of the resultant sulfonylurea product, in the same way, 114 mg (yield 33%: 3 steps) of the above-identified compound was obtained. Properties: colorless crystal, Melting point: >200° C. (decomposition), PMR (δ ppm, DMSO-d$_6$): 7.11 (1H, s), 7.19 (1H, d), 7.24 (1H, d), 7.86 (1H, d), 8.20 (1H, d), 8.56 (1H, s), 11.57 (1H, s).

Preparation Example 22

Synthesis of 3-(3-acetamide-4-methoxybenzenesulfonyl)-7-chloro-2,4(1H,3H)-quinazolinedione (Compound 22)

500 mg (2.19 mmol) of 3-acetamide-4-methoxybenzenesulfonamide and 836 mg (2.19 mmol) of benzyl 4-chloro-2-N-phenoxycarbonylanthranilate were treated in the same way as in Preparation Example 8 to obtain 812 mg (yield 70%) of benzyl 2-{[(3-acetylamino-4-methoxybenzenesulfonylamino)carbonyl]amino}-4-chlorobenzoate. Properties: colorless amorphous, PMR (δ ppm, DMSO-d$_6$): 2.12 (3H, s), 3.93 (3H, s), 5.36 (2H, s), 7.20 (1H, d), 7.24 (1H, d), 7.36–7.48 (5H, m), 7.69 (1H, d), 7.96 (1H, d), 8.24 (1H, s), 8.67 (1H, s), 9.39 (1H, s), 10.25 (1H, s), 12.11 (1H, br).

Then, from 611 mg (1.09 mmol) of the resultant sulfonylurea product, in the same way, 250 mg (yield 39%: 2 steps) of the above-identified compound was obtained. Properties: colorless crystal, Melting point: >200° C. (decomposition), PMR (δ ppm, DMSO-d$_6$): 2.12 (3H, s), 3.95 (3H, s), 7.12 (1H, s), 7.23 (1H, d), 7.30 (1H, d), 7.85 (1H, d), 7.89 (1H, d), 8.80 (1H, s), 9.42 (1H, s), 11.59 (1H, br).

Preparation Example 23

Synthesis of 3-(3-amino-4-methoxybenzenesulfonyl)-7-chloro-2,4(1H,3H)-quinazolinedione (Compound 23)

400 mg (1.40 mmol) of 3-t-butoxycarbonylamino-4-methoxybenzenesulfonamide and 533 mg (1.40 mmol) of benzyl 4-chloro-2-N-phenoxycarbonylanthranilate were treated in the same way as in Preparation Example 17 to obtain 86 mg (yield 16%: 4 steps) of the above-identified compound. Properties: colorless crystal, Melting point: >200° C. (decomposition), PMR (δ ppm, DMSO-d$_6$): 3.81 (3H, s), 7.26–7.37 (5H, m), 7.77 (1H, s), 7.90 (1H, d), 7.94 (1H, d), 11.73 (1H, s).

Preparation Example 24

Synthesis of 7-chloro-3-(4-methoxy-3-methylsulfonylaminobenzenesulfonyl)-2,4(1H,3H)-quinazolinedione (Compound 24)

500 mg (1.89 mmol) of 4-methoxy-3-methylsulfonylaminobenzenesulfonamide and 722 mg (1.89 mmol) of benzyl 4-chloro-2-N-phenoxycarbonylanthranilate were treated in the same way as in Preparation Example 8 to obtain 888 mg (yield 83%) of benzyl 2-({[[(4-methoxy-3-methylsulfonylamino)benzenesulfonylamino]carbonyl}amino)-4-chlorobenzoate. Properties: colorless amorphous, PMR (δ ppm, DMSO-d$_6$): 2.12 (3H, s), 3.93 (3H, s), 5.36 (2H, s), 7.20 (1H, d), 7.24 (1H, d), 7.36–7.48 (5H, m), 7.69 (1H, d), 7.96 (1H, d), 8.24 (1H, s), 8.67 (1H, s), 9.39 (1H, s), 10.25 (1H, s), 12.11 (1H, br).

Then, from 880 mg (1.55 mmol) of the resultant sulfonylurea product, in the same way, 620 mg (yield 85%: 2 steps) of the above-identified compound was obtained. Properties: colorless crystal, Melting point: >200° C. (decomposition), PMR (δ ppm, DMSO-d$_6$): 3.04 (3H, s), 3.94 (3H, s), 7.11 (1H, s), 7.23 (1H, d), 7.34 (1H, d), 7.86 (1H, d), 7.99 (1H, d), 8.10 (1H, s).

Preparation Example 25

Synthesis of 4-[(7-chloro-2,4(1H,3H)-quinazolinedion-3-yl)sulfonyl]-1-hydroxy-nanhthalene-2-carboxylic acid (Compound 25)

323 mg (1.00 mmol) of 3-t-butoxycarbonyl-4-hydroxy-1-naphthalenesulfonamide and 381 mg (1.00 mmol) of benzyl 4-chloro-2-N-phenoxycarbonylanthranilate were treated in the same way as in Preparation Example 17 to obtain 447 mg (yield 73%) of 4-({[(2-benzyloxycarbonyl-5-chloroanilino)carbonyl]amino}sulfonyl)-1-hydroxy-2-naphthalenecarboxylic acid t-butyl ester. Properties: colorless amorphous, PMR (δ ppm, DMSO-d$_6$): 1.66 (9H, s), 5.34 (3H, s), 6.98 (1H, d), 7.35–7.48 (5H, m), 7.66 (1H, m), 7.81 (1H, m), 7.89 (1H, d), 8.37 (2H, m), 8.44 (1H, s), 8.71 (1H, d), 10.02 (1H, br), 12.52 (1H, br).

Then, from 445 mg (0.72 mmol) of the resultant sulfonylurea product, in the same way, 56 mg (yield 18%: 3 steps) of the above-identified compound was obtained. Properties: colorless crystal, Melting point: >200° C. (decomposition), PMR (δ ppm, DMSO-d$_6$): 7.08 (1H, s), 7.20 (1H, d), 7.63 (1H, t), 7.77 (1H, t), 7.84 (1H, d), 8.42 (1H, d), 8.51 (1H, d), 8.75 (1H, s), 11.57 (1H, s).

Preparation Example 26

Synthesis of 5-[(7-chloro-2,4(1H,3H)-quinazolinedion-3-yl)sulfonyl]anthranilic acid (Compound 26)

834 mg (2.05 mmol) of 4-benzyloxycarbonylamino-3-t-butoxycarbonylbenzenesulfonamide and 783 mg (2.05 mmol) of benzyl 4-chloro-2-N-phenoxycarbonylanthranilate were treated in the same way as in Preparation Example 17 to obtain 1.18 g (yield 83%) of benzyl 2-{[(4-benzyloxycarbonylamino-3-t-butoxycarbonylbenzenesulfonylamino)carbonyl]amino}-4-chlorobenzoate. Properties: colorless amorphous, PMR (δ ppm, CDCl$_3$): 1.56 (9H, s), 5.22 (2H, s), 5.37 (2H, s), 7.04 (1H, dd), 7.33–7.42 (10H, m), 7.97 (1H, d), 8.14 (1H, d), 8.45 (1H, d), 8.60 (1H, d), 8.65 (1H, d), 11.01 (1H, s), 11.11 (1H, s).

Then, from 1.17 g (1.69 mmol) of the resultant sulfonylurea product, in the same way, 404 mg (yield 60%: 3 steps) of the above-identified compound was obtained. Properties: colorless crystal, Melting point; >200° C. (decomposition), PMR (δ ppm, DMSO-d$_6$): 6.89 (1H, d), 7.11 (1H, s), 7.23 (1H, d), 7.85 (1H, d), 7.98 (1H, d), 8.51 (1H, s), 11.51 (1H, s).

Preparation Example 27

Synthesis of 4-[(7-methoxy-2,4(1H,3H)-quinazolinedion-3-yl)sulfonyl]anthranilic acid (Compound 27)

500 mg (1.23 mmol) of 3-benzyloxycarbonylamino-4-t-butoxycarbonylbenzenesulfonamide and 460 mg (1.22 mmol) of benzyl 4-methoxy-2-N-phenoxycarbonylanthranilate were treated in the same way as in Preparation Example 17 to obtain 15 mg (yield 3.1%: 4 steps) of the above-identified compound. Properties: colorless crystal, Melting point: >200° C. (decomposition), PMR (δ ppm, DMSO-$d_6$): 3.82 (3H, s), 6.58 (1H, s), 6.80 (1H, d), 7.16 (1H, d), 7.56 (1H, s), 7.80 (1H, d), 7.90 (1H, d), 11.49 (1H, s).

Preparation Example 28

Synthesis of (±)-7-[(7-chloro-2,4(1H,3H)-guinazolinedion-3-yl)sulfonyl]-2-oxo-1H,3H-quinoline-3-carboxylic acid (Compound 28)

400 mg (1.23 mmol) of (±)-3-t-butoxycarbonyl-2-oxo-1H,3H-quinoline-7-sulfonamide and 468 mg (1.23 mmol) of benzyl 4-chloro-2-N-phenoxycarbonylanthranilate were treated in the same way as in Preparation Example 17 to obtain 649 mg (yield 86%) of 8-({[(2-benzyloxycarbonyl-5-chloroanilino)carbonyl]amino}sulfonyl)-2-oxo-1,2,3,4-tetrahydro-3-quinoline carboxylic acid t-butyl ester. Properties: colorless amorphous, PMR (δ ppm, $CDC_{l3}$): 1.32 (9H, s), 3.18–3.30 (2H, m), 3.54 (1H, s), 5.35 (2H, s), 6.85 (1H, m), 7.00 (1H, m), 7.35–7.39 (5H, m), 7.87–7.96 (3H, m), 8.47 (1H, m), 8.78 (1H, br), 10.92 (1H, br).

Then, from 640 mg (1.04 mmol) of the resultant sulfonylurea product, in the same way, 258 mg (yield 55%: 3 steps) of the above-identified compound was obtained. Properties: colorless crystal, Melting point: >200° C. (decomposition), PMR (δ ppm, DMSO-$d_6$): 3.23–3.31 (2H, m), 3.59 (1H, t), 7.07 (1H, d), 7.12 (1H, s), 7.25 (1H, d), 7.86 (1H, d), 7.96 (1H, d), 7.98 (1H, d), 10.84 (1H, s), 11.60 (1H, s).

Preparation Example 29

Synthesis of (±)-6-[(7-chloro-2,4(1H,3H)-guinazolinedion-3-yl)sulfonyl]-3-oxo-1,4-benzoxazine-2-carboxylic acid (Compound 29)

300 mg (0.91 mmol) of (±)-2-t-butoxycarbonyl-3-oxo-1,4-benzoxazin-6-sulfonamide and 349 mg (0.91 mmol) of benzyl 4-chloro-2-N phenoxycarbonylanthranilate were treated in the same way as in Preparation Example 17 to obtain 417 mg (yield 74%) of 5-({[(2-benzyloxycarbonyl-5-chloroanilino)carbonyl]amino}sulfonyl)-3-oxo-3,4-dihydro-2H-1,4-benzoxazine-2-carboxylic acid t-butyl ester. Properties: colorless amorphous, PMR (δ ppm, DMSO-$d_6$): 1.29 (9H, s), 5.37 (2H, s), 5.42 (2H, s), 7.19–7.26 (2H, m), 7.37–7.57 (7H, m), 7.97 (1H, d), 8.25 (1H, d), 10.27 (1H, s), 11.25 (1H, s), 12.22 (1H, br).

Then, from 417 mg (0.68 mmol) of the resultant sulfonylurea product, in the same way, 100 mg (yield 32%: 3 steps) of the above-identified compound was obtained. Properties: colorless crystal, Melting point: >200° C. (decomposition), PMR (δ ppm, DMSO-$d_6$): 5.47 (1H, s), 7.11 (1H, s), 7.24 (1H, d), 7.29 (1H, d), 7.76 (1H, s), 7.78 (1H, d), 7.86 (1H, d), 11.25 (1H, s), 11.62 (1H, s).

Preparation Example 30

Synthesis of 4-[(7-hydroxy-2,4(1H,3H)-guinazolinedion-3-yl)sulfonyl]anthranilic acid (Compound 30)

620 mg (1.53 mmol) of 3-benzyloxycarbonylamino-4-t-butoxycarbonylbenzenesulfonamide and 550 mg (1.51 mmol) of benzyl 4-hydroxy-2-N-phenoxy-carbonylanthranilate were treated in the same way as in Preparation Example 17 to obtain 25 mg (yield 4%: 4 steps) of the above-identified compound. Properties: colorless crystal, Melting point: >200° C. (decomposition), PMR (δ ppm, DMSO-$d_6$): 6.48 (1H, s), 6.61 (1H, d), 7.14 (1H, d), 7.51 (1H, s), 7.70 (1H, d), 7.90 (1H, d), 10.80 (1H, s), 11.39 (1H, s).

Preparation Example 31

Synthesis of 4-[(7-chloro-2,4(1H,3H-guinazolinedion-3-yl)sulfonyl]-2-N-propionylanthranilic acid (Compound 31)

840 mg (1.86 mmol) of Compound 17 was dissolved in 8 ml of 1,4-dioxane, 240 μl (2.79 mmol) of propionyl chloride was added dropwise, then the resultant mixture was stirred overnight at 60° C. An excess of water was added to the reaction solution and the mixture was extracted with ethyl acetate. The organic layer thus obtained was washed, dried, and concentrated to obtain a crude product of t-butyl 4-[(7-chloro-2,4(1H,3H)-quinazolinedion-3-yl)sulfonyl]-2-N-propionylanthranilate. The obtained crude product was stirred at room temperature in 3 ml of trifluoroacetic acid for 1 hour, then the reaction solution was concentrated in vacuo to obtain a crude product. This was washed by diethyl ether to obtain 400 mg (yield 48%: 2 steps) of the above-identified compound. Properties: colorless crystal, Melting point: >200° C. (decomposition), PMR (δ ppm, DMSO-$d_6$): 1.10 (3H, t), 2.45 (2H, dd), 7.11 (1H, s), 7.24 (1H, d), 7.85 (1H, d), 7.88 (1H, d), 8.17 (1H, d), 9.18 (1H, s), 11.07 (1H, s), 11.63 (1H, s).

Preparation Example 32

Synthesis of 4-[(6-chloro-2,4(1H,3H)-guinazolinedion-3-yl)sulfonyl]anthranilic acid (Compound 32)

300 mg (0.74 mmol) of 3-benzyloxycarbonylamino-4-t-butoxycarbonylbenzenesulfonamide and 310 mg (0.81 mmol) of benzyl 5-chloro-2-N-phenoxycarbonylanthranilate were treated in the same way as in Preparation Example 17 to obtain 75 mg (yield 26%: 4 steps) of the above-identified compound. Properties: colorless crystal, Melting point: >200° C. (decomposition), PMR (δ ppm, DMSO-$d_6$): 7.13–7.20 (2H, m), 7.56 (1H, s), 7.72 (1H, d), 7.82 (1H, s), 7.90 (1H, d), 11.68 (1H, s).

Preparation Example 33

Synthesis of 4-[(7-chloro-2,4(1H,3H)-quinazolinedion-3-yl)sulfonyl]-2-N-methanesulfonylanthranilic acid (Compound 33)

200 mg (0.44 mmol) of Compound 17 was treated in the same way as in Preparation Example 3 to obtain 81 mg of t-butyl 4-[(7-chloro-2,4(1H,3H)-quinazolinedion-3-yl)sulfonyl]-2-N-methanesulfonylanthranilate. This was used to perform the same debutylation reaction to obtain 53 mg (yield 25%: 2 steps) of the above-identified compound. Properties: colorless crystal, Melting point: >200° C. (decomposition), PMR (δ ppm, DMSO-$d_6$): 3.24 (3H, s), 7.11 (1H, s), 7.25 (1H, d), 7.85–7.91 (2H, m), 8.23 (1H, d), 8.39 (1H, s), 11.05 (1H, br), 11.70 (1H, s).

Preparation Example 34

Synthesis of 3-(3-aminobenzenesulfonyl)-7-chloro-2,4-(1H,3H)quinazolinedion methanesulfonic acid salt (Compound 34)

2.15 g (6.10 mmol) of compound 12 was dissolved in 65 ml of THF and 0.4 ml of methanesulfonic acid was added dropwise. To this solution, 200 ml of ether was added and the resultant precipate was filtered to obtain 2.59 g (yield 95%) of the above-identified compound. Properties: colorless amorphous, PMR (δ ppm, DMSO-$d_6$): 2.35 (3H, s), 6.98 (1H, d), 7.12 (1H, m), 7.25 (1H, m), 7.34 (2H, s), 7.43 (1H, m), 7.86 (1H, s), 11.64 (1H, s).

Example 1

Measurement of Chymase Inhibitory Activity

Human heart chymase was purified according to the method of Urata et al. (*J. Biol. Chem.*, 1990, 265, 22348). The inhibitory activity of the compound of the present invention was determined as follows. Purified enzyme was diluted with 0.1M tris-HCl buffer (pH=7.5), 1M sodium chloride, and 0.01% TritonX-100 to obtain an enzyme solution having appropriate concentrations. Suc-Ala-Ala-Pro-Phe-MCA (Peptide Institute Inc.) was dissolved in 10 mM dimethyl sulfoxide (hereinafter referred to as DMSO) and diluted 20-fold with 0.1M Tris-HCl buffer (pH 7.5) containing 1M sodium chloride and 0.01% TritonX-100 to an appropriate concentration to prepare substrate solution.

5 μl of the test sample in DMSO was added to 75 μl of the enzyme solution and preincubated at 30° C. for 10 minutes. Then, 20 μl of the substrate solution was added to the test sample-enzyme mixture, and incubated at 30° C. Ten minutes later, 50 μl of 30% acetic acid was added to stop the enzymatic reaction, and the amount of AMC formed was determined using a fluorophotometer. At the same time, 5 μl of DMSO in stead of the test sample was added and reacted simultaneously as a control. The inhibitory activity to human chymase was calculated based on the value of the control, and then the inhibition percentage and the 50% inhibition concentration ($IC_{50}$) were determined.

The $IC_{50}$ values for representative compounds are shown in Table I.

TABLE I

| Example No. | $IC_{50}$ value (μM) |
| --- | --- |
| 1 | 0.36 |
| 2 | 0.14 |
| 8 | 0.035 |
| 10 | 0.17 |
| 12 | 0.44 |
| 13 | 0.3 |
| 16 | 0.84 |
| 17 | 0.14 |
| 18 | 0.14 |
| 21 | 0.34 |
| 22 | 0.3 |
| 24 | 0.32 |
| 27 | 4.0 |
| 29 | 1.7 |
| 32 | 1.5 |
| 34 | 0.36 |

Example 2

Effects of Chymase Inhibitor on Increase in Eosinophils of Mice Infected with *Nippostrongylus brasiliensis* (Nb)

Male BALB/c mice (7-weeks old) were transcutaneously inflected with 750 parasitic worms of *Nippostrongylus brasiliensis* (Nb) (third stage larvae) in accordance with an already reported method (*Int. Arch. Allergy Immunol.* 117, Suppl. 1, 2, 1998). After two weeks, the number of eosinophils in the peripheral blood and the total number of leukocytes in the peripheral blood were measured. Further, at day 7 and day 10, the number of eggs in the feces was measured. The chymase inhibitor (Compound 18) was dissolved in saline and injected intraperitoneally in 0.2 ml amounts once a day continuously from the day before infection until the end of the test. Note that the control group was administered only saline. The number of cells in the peripheral blood was measured by sampling peripheral blood from the eye cavity. The eosinophils were stained with a Hinkelman's solution, then counted under a microscope. Further, the total number of leukocytes was measured under a microscope after staining with by a Turk's solution. The number of eggs in the feces was determined by obtaining individual feces of the mice, measuring their weight, then dissolving them in 1 ml of 10% formalin, counting the number of eggs in the feces solution under a microscope, then expressing the result as the number of eggs per gram of feces.

Results

Infection of mice with Nb increased remarkably the number of eosinophils in the peripheral blood 2 weeks after the infection (Table II). Administration of a chymase inhibitor (Compound 18) at dose of 50 mg/kg/day significantly suppressed the Nb-induced increase in the number of eosinophils (Dunnett's test). Since the administration of Compound 18 had little effect on the total number of leukocytes in the peripheral blood (Table II), it was shown that the action of Compound 18 is specific for eosinophils. Further, almost no difference was observed between the group administered Compound 18 and the group not administered it in the number of eggs of Nb on day 7 or day 10 after Nb infection (Table III), suggesting that compound 18 affects neither infectivity nor expulsion of Nb in mice. Taken together, these resuts show that administration of chymase inhibitor significantly suppresses parasite-induced eosinophilia in mice, and suggest that chymase inhibitor is useful in the prevention or treatment for alleviating conditions in a variety of diseases in which eosinophils are involved.

Formulation Example 1

Production of Tablets 100.0 g of Compound 1 was mixed with microcrystalline cellulose in an amount of 22.5 g and magnesium stearate in an amount of 2.5 g and then tabletized by a single-action type tabletizing machine to produce tablets each containing 200 mg of Compound 1 and having a diameter of 9 mm and a weight of 250 mg.

Formulation Example 2

Production of Granules 30 g of Compound 1 was mixed well with lactose in an amount of 265 g and magnesium stearate in an amount of 5 g. The mixture was pressed molded, then pulverized and the granules sieved to obtain excellent 10% granules of 20 to 50 mesh.

Formulation Example 3

Production of Suppository

Vitepsol H-15 (made by Dynamite Nobel Co.) was warmed to melt. To this was added Compound 1 to a concentration of 12.5 mg/ml. This was homogeneously mixed, then was added in 2 ml amounts to a rectal supposi-

TABLE II

Effects of Chymase Inhibitor (Compound 18)
on Number of Eosinophils and Total Number of Leukocytes
in Peripheral Blood in Nb Infected Mice

| Compound 18 | Number of eosinophils in peripheral blood (no./mm$^3$) | | | Total no. of leukocytes in peripheral blood 2 weeks after infection (no./mm$^3$) |
|---|---|---|---|---|
| | Before infection | 2 weeks after infection | P | |
| 0 | 30 ± 29 | 1036 ± 158 | | 6180 ± 1660 |
| 2 mg/kg | 30 ± 12 | 1036 ± 240 | NS | |
| 10 mg/kg | 36 ± 11 | 818 ± 155 | NS | |
| 50 mg/kg | 32 ± 16 | 360 ± 66 | <0.001 | 5820 ± 460 |

TABLE III

Effects of Chymase Inhibitor (Compound
18) on Number of Eggs in Feces in Nb Infected Mice

| | No. of Nb eggs in gram of feces | |
|---|---|---|
| Compound 18 | Day 7 | Day 10 |
| 0 | 27139 ± 6375 | 800 ± 1789 |
| 50 mg/kg | 30541 ± 12501 | 558 ± 1248 |

INDUSTRIAL APPLICABILITY

According to the present invention, chymase inhibitor can effectively prevent or treat a condition of various diseases in which it is known that eosinophils increase through its effect in suppressing an increase in eosinophils.

What is claimed is:

1. A method for the treatment of a disease involving an increase of eosinophils comprising administering to a patient in need of such treatment a chymase inhibitor in an amount effective for treatment of said disease, wherein the chymase inhibitor is a quinazoline derivative having the following formula (I) or a pharmaceutically acceptable salt thereof:

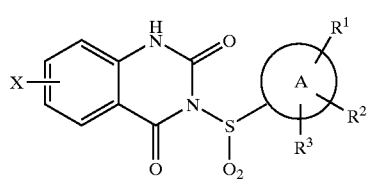

(I)

wherein the ring A represents an aryl group;

$R^1$ represents a hydroxyl group, an amino group, a $C_1$ to $C_4$ lower alkylamino group which may optionally be substituted with a carboxylic acid group, a $C_7$ to $C_{10}$ lower aralkylamino group which may optionally be substituted with a carboxylic acid group, an amino group acylated with a $C_1$ to $C_4$ lower aliphatic acid which may optionally be substituted with a carboxylic acid group, an amino group acylated with an aromatic ring carboxylic acid which may optionally be substituted with a carboxylic acid group, an amino group acylated with a heteroaromatic ring carboxylic acid which may optionally be substituted with a carboxylic acid group, wherein the heteroaromatic ring is selected from pyridine and pyrrole, an amino group sulfonylated with a $C_1$ to $C_4$ lower alkanesulfonic acid which may optionally be substituted with a carboxylic acid group, an amino group sulfonylated with an aromatic ring sulfonic acid which may optionally be substituted with a carboxylic acid group, an amino group sulfonylated with a heteroaromatic ring sulfonic acid which may optionally be substituted with a carboxylic acid group, wherein the heteroaromatic ring is selected from pyridine and pyrrole, a $C_1$ to $C_4$ lower alkyl group substituted with a carboxylic acid group, or a $C_2$ to $C_4$ lower alkylene group which may optionally be substituted with a carboxylic acid group;

$R^2$ and $R^3$ may be the same or different and represent a hydrogen atom, an unsubstituted or substituted $C_1$ to $C_4$ lower alkyl group, a halogen atom, a hydroxyl group, a $C_1$ to $C_4$ lower alkoxyl group, an amino group, a $C_1$ to $C_4$ lower alkylamino group which may optionally be substituted with a carboxylic acid group, a halogen atom, or a $C_1$ to $C_4$ lower alkoxyl group, a $C_7$ to $C_{10}$ aralkylamino group which may optionally be substituted with a carboxylic acid group, a halogen atom, or a $C_1$ to $C_4$ lower alkoxyl group, an amino group acylated with a $C_1$ to $C_4$ lower aliphatic acid which may optionally be substituted with a carboxylic acid group, an amino group acylated with an aromatic ring carboxylic acid which may optionally be substituted with a carboxylic acid group, an amino group acylated with a heteroaromatic ring carboxylic acid which may optionally be substituted with a carboxylic acid group, wherein the heteroaromatic ring is selected form pyridine and pyrrole, an amino group sulfonylated with a $C_1$ to $C_4$ lower alkanesulfonic acid which may optionally be substituted with a carboxylic acid group, an amino group sulfonylated with an aromatic ring sulfonic acid which may optionally be substituted with a carboxylic acid group, an amino group sulfonylated with a heteroaromatic ring sulfonic acid which may optionally be substituted with a carboxylic acid group, wherein the heteroaromatic ring is selected from pyridine and pyrrole, or a carboxylic acid group or when the ring A is a benzene ring, $R^1$ and $R^2$ may form, together with the substituting benzene ring, a fused heterocyclic ring selected from the group consisting of a tetrahydroquinoline ring and a benzoxazine ring, which may optionally be substituted with a carboxylic acid and in which the carbon atom in the ring may form a carbonyl group and $R^3$ is the same as defined above; and X represents a hydrogen atom, a $C_1$ to $C_4$ lower alkyl group, a $C_1$ to $C_4$ lower alkoxy group, a halogen atom, a hydroxyl group, an amino group, or a nitro group.

2. A method according to claim 1, wherein the aryl group represented by the ring A is selected from the group consisting of a benzene ring and a naphthalene ring.

3. A method according to claim 1, wherein the $C_1$ to $C_4$ lower alkylamino group which may optionally be substituted with the carboxylic acid group is selected from the group consisting of a methylamino group, an ethylamino group, a propylamino group, a butylamino group, a carboxymethylamino group, a carboxyethylamino group, a carboxypropylamino group, and a carboxybutylamino group.

4. A method according to claim 1, wherein the $C_7$ to $C_{12}$ lower aralkylamino group which may be substituted with the carboxylic acid group represented by $R^1$ is selected from the group consisting of a benzylamino group, a phenetylamino group, a phenylpropylamino group, a phenylbutylamino group, a carboxybenzylamino group, a carboxyphenetylamino group, a carboxyphenylpropylamino group, and a carboxyphenylbutylamino group.

5. A method according to claim 1, wherein the amino group acylated with a $C_1$ to $C_4$ lower aliphatic acid which may be substituted with a carboxylic acid group, the amino group acylated with an aromatic ring carboxylic acid which may be substituted with a carboxylic acid group, and the amino group acylated with a heteroaromatic ring carboxylic acid which may be substituted with a carboxylic acid group represented by $R^1$ are each independently selected from the group consisting of a formylamino group, an acetylamino group, a propionylamino group, a butyrylamino group; a benzoylamino group, a naphthoylamino group, a pyridinecarbonylamino group, a pyrrolecarbonylamino group, a carboxyacetylamino group, a carboxypropionylamino group, a carboxybutyrylamino group, a carboxybenzoylamino group, a carboxynaphthoylamino group, a carboxypyridinecarbonylamino group, and a carboxypyrrolecarbonylamino group.

6. A method according to claim 1, wherein the amino group sulfonylated with a $C_1$ to $C_4$ lower alkanesulfonic acid which may be substituted with a carboxylic acid group, the amino group sulfonylated with air aromatic ring sulfonic acid which may be substituted with a carboxylic acid group, and the amino group sulfonylated with a heteroaromatic ring sulfonic acid which may be substituted with a carboxylic acid group represented by $R^1$ are each independently selected from the group consisting of
a methanesulfonylamino group, an ethanesulfonylamino group, a propanesulfonylamino group, a butanesulfonylamino group, a benzenesulfonylamino group, a naphthalenesulfonylamino group, a pyridinesulfonylamino group, a pyrrolesulfonylamino group, a carboxymethanesulfonylamino group, a carboxyethanesulfonylamino group, a carboxypropanesulfonylamino group, a carboxybutane-sulfonylamino group, a carboxybenzenesulfonylamino group, a carboxynaphthalenesulfonylamino group, a carboxypyridinesulfonylamino group, and a carboxypyrrolesulfonylamino group.

7. A method according to claim 1, wherein the $C_1$ to $C_4$ lower alkyl group substituted with a carboxylic acid group represented by $R^1$ is selected from the group consisting of an acetic acid group, a propionic acid group, a butyric acid group, and a valeric acid group.

8. A method according to claim 1, wherein the $C_2$ to $C_4$ lower alkylene group substituted with a carboxylic acid group represented by $R^1$ is selected from the group consisting of an acrylic acid group and a crotonic acid group.

9. A method according to claim 1, wherein the unsubstituted or substituted $C_1$ to $C_4$ lower alkyl group represented by $R^2$ or $R^3$ is selected from the group consisting of a straight-chain alkyl group and a branched alkyl group.

10. A method according to claim 9, wherein the branched alkyl group is selected from the group consisting of an isopropyl group, a sec-butyl group, and a t-butyl group.

11. A method according to claim 1, wherein the substituent group of the $C_1$ to $C_4$ lower alkyl group is selected from the group consisting of a carboxylic acid group, a halogen atom, a $C_1$ to $C_4$ lower alkoxy group, an amino group, a methylamino group, a dimethylamino group, a carboxymethylamino group, and a carboxyethylamino group.

12. A method according to claim 1, wherein the halogen atom represented by $R^2$ or $R^3$ is selected from the group consisting of a fluorine atom, a chlorine atom, a bromine atom and an iodine atom.

13. A method according to claim 1, wherein the $C_1$ to $C_4$ lower alkoxyl group represented by $R^2$ or $R^3$ is selected from the group consisting of a straight-chain alkyloxy group and a branched alkyloxy group.

14. A method according to claim 13, wherein the straight-chain alkyloxy group is selected from the group consisting of a methoxy group, an ethoxy group, a n-propyloxy group, and a n-butoxy group.

15. A method according to claim 13, wherein the branched alkyloxy group is selected from the group consisting of an isopropyloxy group, a sec-butoxy group, and a t-butoxy group.

16. A method according to claim 1, wherein the unsubstituted or substituted $C_1$ to $C_4$ lower alkylamino group represented by $R^2$ or $R^3$ is selected from the group consisting of a methylamino group, an ethylamino group, a propylamino group, and a butylamino group.

17. A method according to claim 1, wherein the substituent group of the $C_1$ to $C_4$ lower alkylamino group is selected from the group consisting of a carboxylic acid group, a halogen atom, and a $C_1$ to $C_4$ lower alkoxyl group.

18. A method according to claim 1, wherein the unsubstituted or substituted $C_7$ to $C_{12}$ lower aralkylamino group represented by $R^2$ or $R^3$ is selected from the group consisting of a benzylamino group, a phenetylamino group, a phenylpropylamino group, and a phenylbutylamino group.

19. A method according to claim 1, wherein the substituent group of the aralkylamino group is selected from the group consisting of a carboxylic acid group, a halogen atom, and a $C_1$ to $C_4$ lower alkoxyl group.

20. A method according to claim 1, wherein the amino group acylated with a $C_1$ to $C_4$ lower aliphatic acid which may be substituted with a carboxylic acid group, the amino group acylated with an aromatic ring carboxylic acid which may be substituted with a carboxylic acid group, and the amino group acylated with a heteroaromatic ring carboxylic acid which may be substituted with a carboxylic acid group represented by $R^2$ or $R^3$ are each independently selected from the group consisting of a formylamino group, an acetylamino group, a propionylamino group, a butyrylamino group, a benzoylamino group, a naphthoylamino group, a pyridinecarbonylamino group, a pyrrolecarbonylamino group, a carboxyacetylamino group, a carboxypropionylamino group, a carboxybutyrylamino group, a carboxybenzoylamino group, a carboxynaphthoylamino group, a carboxypyridinecarbonylamino group, and a carboxypyrrolecarbonylamino group.

21. A method according to claim 1, wherein the amino group sulfonylated with a $C_1$ to $C_4$ lower alkanesulfonic acid which may be substituted with a carboxylic acid group, the amino group sulfonylated with an aromatic ring sulfonic acid which may be substituted with a carboxylic acid group, and the amino group sulfonylated with a heteroaromatic ring sulfonic acid which may be substituted with a carboxylic acid group represented by $R^2$ or $R^3$ are each independently selected from the group consisting of a methanesulfonylamino group, an ethanesulfonylamino group, a propanesulfonylamino group, a benzenesulfonylamino group, a naphthalenesulfonylamino group, a pyridinesulfonylamino group, a pyrrolesulfonylamino group, a carboxymethanesulfonylamino group, a carboxyethanesulfonylamino group, a carboxypropanesulfonylamino group, a carboxybenzenesulfonylamino group, a carboxynaphthalenesulfonylamino group, a carboxypyridine-sulfonylamino group, and a carboxypyrrolesulfonylamino group.

22. A method according to claim 1, wherein the fused heterocyclic ring which may be substituted with a carboxylic acid and in which the carbon atom in the ring may form a carbonyl group which $R^1$ and $R^2$ form together with the substituting benzene ring when the ring A is a benzene ring, is selected from the group consisting of a tetrahydroquinoline, a benzoxazine, a quinoxaline, a benzodioxane, a carboxytetrahydroquinoline, a carboxybenzoxazine, a carboxyquinoxaline, and a carboxybenzodioxane.

23. A method according to claim 1, wherein the $C_1$ to $C_4$ lower alkyl group represented by X is selected from the group consisting of a methyl group, an ethyl group, a n-propyl group, a n-butyl group, an isopropyl group, a sec-butyl group, and a t-butyl group.

24. A method according to claim 1, wherein the $C_1$ to $C_4$ lower alkoxyl group represented by X is selected from the group consisting of a methoxy group, an ethoxy group, a n-propyloxy group, a n-butoxy group, an isopropyloxy group, a sec-butoxy group, and a t-butoxy group.

25. A method according to claim 1, wherein the halogen atom represented by X, is selected from the group consisting of a fluorine atom, a chlorine atom, a bromine atom and an iodine atom.

26. A method according to claim 1, wherein the pharmaceutically acceptable salt is selected from the group consisting of an acid salt and an alkali metal salt.

27. A method according to claim 26, wherein the pharmaceutically acceptable salt is selected from the group consisting of a hydrochloric acid salt, a methanesulfonic acid salt, a trifluoroacetic acid salt, a sodium salt and a potassium salt.

28. A method for treating an allergic disease comprising administering to a patient in need of such treatment a chymase inhibitor in an amount effective for suppressing an increase in eosinophils, thereby treating said allergic disease wherein the chymase inhibitor is a quinazoline derivative having the following formula (I) or a pharmaceutically acceptable salt thereof:

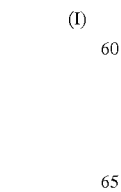

(I)

wherein the ring A represents an aryl group;

$R^1$ represents a hydroxyl group, an amino group, a $C_1$ to $C_4$ lower alkylamino group which may optionally be substituted with a carboxylic acid group, a $C_7$ to $C_{10}$ lower aralkylamino group which may optionally be substituted with a carboxylic acid group, an amino group acylated with a $C_1$ to $C_4$ lower aliphatic acid which may optionally be substituted with a carboxylic acid group, an amino group acylated with an aromatic ring carboxylic acid which may optionally be substituted with a carboxylic acid group, an amino group acylated with a heteroaromatic ring carboxylic acid which may optionally be substituted with a carboxylic acid group, wherein the heteroaromatic ring is selected from pyridine and pyrrole, an amino group sulfonylated with a $C_1$ to $C_4$ lower alkanesulfonic acid which may optionally be substituted with a carboxylic acid group, an amino group sulfonylated with an aromatic ring sulfonic acid which may optionally be substituted with a carboxylic acid group, an amino group sulfonylated with a heteroaromatic ring sulfonic acid which may optionally be substituted with a carboxylic acid group, wherein the heteroaromatic ring is selected form pyridine and pyrrole, a $C_1$ to $C_4$ lower alkyl group substituted with a carboxylic acid group, or a $C_2$ to $C_4$ lower alkylene group which may optionally be substituted with a carboxylic acid group;

$R^2$ and $R^3$ may be the same or different and represent a hydrogen atom, an unsubstituted or substituted $C_1$ to $C_4$ lower alkyl group, a halogen atom, a hydroxyl group, a $C_1$ to $C_4$ lower alkoxyl group, an amino group, a $C_1$ to $C_4$ lower alkylamino group which may optionally be substituted with a carboxylic acid group, a halogen atom, or a $C_1$ to $C_4$ lower alkoxyl group, a $C_7$ to $C_{10}$ aralkylamino group which may optionally be substituted with a carboxylic acid group, a halogen atom, or a $C_1$ to $C_4$ lower alkoxyl group, an amino group acylated with a $C_1$ to $C_4$ lower aliphatic acid which may optionally be substituted with a carboxylic acid group, an amino group acylated with an aromatic ring carboxylic acid which may optionally be substituted with a carboxylic acid group, an amino group acylated with a heteroaromatic ring carboxylic acid which may optionally be substituted with a carboxylic acid group, wherein the heteroaromatic ring is selected form pyridine and pyrrole, an amino group sulfonylated with a $C_1$ to $C_4$ lower alkanesulfonic acid which may optionally be substituted with a carboxylic acid group, an amino group sulfonylated with an aromatic ring sulfonic acid which may optionally be substituted with a carboxylic acid group, an amino group sulfonylated with a heteroaromatic ring sulfonic acid which may optionally be substituted with a carboxylic acid group, wherein the heteroaromatic ring is selected from pyridine and pyrrole, or a carboxylic acid group or when the ring A is a benzene ring, $R^1$ and $R^2$ may form, together with the substituting benzene ring, a fused heterocyclic ring selected from the group consisting of a tetrahydroquinoline ring and a benzoxazine ring, which may optionally be substituted with a carboxylic acid and in which the carbon atom in the ring may form a carbonyl group and $R^3$ is the same as defined above; and X represents a hydrogen atom, a $C_1$ to $C_4$ lower alkyl group, a $C_1$ to $C_4$ lower alkoxy group, a halogen atom, a hydroxyl group, an amino group, or a nitro group.

29. A method according to claim 28, wherein the aryl group represented by the ring A is selected from the group consisting of a benzene ring and a naphthalene ring.

30. A method according to claim 28, wherein the $C_1$ to $C_4$ lower alkylamino group which may optionally be substituted with the carboxylic acid group is selected from the group consisting of a methylamino group, an ethylamino group, a propylamino group, a butylamino group, a carboxymethylamino group, a carboxyethylamino group, a carboxypropylamino group, and a carboxybutylamino group.

31. A method according to claim 28, wherein the $C_7$ to $C_{12}$ lower aralkylamino group which may be substituted with the carboxylic acid group represented by $R^1$ is selected from the group consisting of a benzylamino group, a phenetylamino group, a phenylpropylamino group, a phenylbutylamino group, a carboxybenzylamino group, a carboxyphenetylamino group, a carboxyphenylpropylamino group, and a carboxyphenylbutylamino group.

32. A method according to claim 28, wherein the amino group acylated with a $C_1$ to $C_4$ lower aliphatic acid which may be substituted with a carboxylic acid group, the ammo group acylated with an aromatic ring carboxylic acid which may be substituted with a carboxylic acid group, and the amino group acylated with a heteroaromatic ring carboxylic acid which may be substituted with a carboxylic acid group represented by $R^1$ are each independently selected from the group consisting of a formylamino group, an acetylamino group, a propionylamino group, a butyrylamino group, a benzoylamino group, a naphthoylamino group, a pyridinecarbonylamino group, a pyrrolecarbonylamino group, a carboxyacetylamino group, a carboxypropionylamino group, a carboxybutyrylamino group, a carboxybenzoylamino group, a carboxynaphthoylamino group, a carboxypyridinecarbonylamino group, and a carboxypyrrolecarbonylamino group.

33. A method according to claim 28, wherein the amino group sulfonylated with a $C_1$ to $C_4$ lower alkanesulfonic acid which may be substituted with a carboxylic acid group, the amino group sulfonylated with an aromatic ring sulfonic acid which may be substituted with a carboxylic acid group, and the amino group sulfonylated with a heteroaromatic ring sulfonic acid which may be substituted with a carboxylic acid group represented by $R^1$ are each independently selected from the group consisting of a methanesulfonylamino group, an ethanesulfonylamino group, a propanesulfonylamino group, a butanesulfonylamino group, a benzenesulfonylamino group, a naphthalenesulfonylamino group, a pyridinesulfonylamino group, a pyrrolesulfonylamino group, a carboxymethanesulfonylamino group, a carboxyethanesulfonylamino group, a carboxypropanesulfonylamino group, a carboxybutane-sulfonylamino group, a carboxybenzenesulfonylamino group, a carboxynaphthalenesulfonylamino group, a carboxypyridinesulfonylamino group, and a carboxypyrrolesulfonylamino group.

34. A method according to claim 28, wherein the $C_1$ to $C_4$ lower alkyl group substituted with a carboxylic acid group represented by $R^1$ is selected from the group consisting of an acetic acid group, a propionic acid group, a butyric acid group, and a valeric acid group.

35. A method according to claim 28, wherein the $C_2$ to $C_4$ lower alkylene group substituted with a carboxylic acid group represented by $R^1$ is selected from the group consisting of an acrylic acid group and a crotonic acid group.

36. A method according to claim 28, wherein the unsubstituted or substituted $C_1$ to $C_4$ lower alkyl group represented by $R^2$ or $R^3$ is selected from the group consisting of a straight-chain alkyl group and a branched alkyl group.

37. A method according to claim 36, wherein the branched alkyl group is selected from the group consisting of an isopropyl group, a sec-butyl group, and a t-butyl group.

38. A method according to claim 28, wherein the substituent group of the $C_1$ to $C_4$ lower alkyl group is selected from the group consisting of a carboxylic acid group, a halogen atom, a $C_1$ to $C_4$ lower alkoxy group, an amino group, a methylamino group, a dimethylamino group, a carboxymethylamino group, and a carboxyethylamino group.

39. A method according to claim 28, wherein the halogen atom represented by $R^2$ or $R^3$ is selected from the group consisting of a fluorine atom, a chlorine atom, a bromine atom and an iodine atom.

40. A method according to claim 28, wherein the $C_1$ to $C_4$ lower alkoxyl group represented by $R^2$ or $R^3$ is selected from the group consisting of a straight-chain alkyloxy group and a branched alkyloxy group.

41. A method according to claim 40, wherein the straight-chain alkyloxy group is selected from the group consisting of a methoxy group, an ethoxy group, a n-propyloxy group, and a n-butoxy group.

42. A method according to claim 40, wherein the branched alkyloxy group is selected from the group consisting of an isopropyloxy group, a sec-butoxy group, and a t-butoxy group.

43. A method according to claim 28, wherein the unsubstituted or substituted $C_1$ to $C_4$ lower alkylamino group represented by $R^2$ or $R^3$ is selected from the group consisting of a methylamino group, an ethylamino group, a propylamino group, and a butylamino group.

44. A method according to claim 28, wherein the substituent group of the $C_1$ to $C_4$ lower alkylamino group is selected from the group consisting of a carboxylic acid group, a halogen atom, and a $C_1$ to $C_4$ lower alkoxyl group.

45. A method according to claim 28, wherein the unsubstituted or substituted $C_7$ to $C_{12}$ lower aralkylamino group represented by $R^2$ or $R^3$ is selected from the group consisting of a benzylamino group, a phenetylamino group, a phenylpropylamino group, and a phenylbutylamino group.

46. A method according to claim 28, wherein the substituent group of the aralkylamino group is selected from the group consisting of a carboxylic acid group, a halogen atom, and a $C_1$ to $C_4$ lower alkoxyl group.

47. A method according to claim 28, wherein the amino group acylated with a $C_1$ to $C_4$ lower aliphatic acid which may be substituted with a carboxylic acid group, the amino group acylated with an aromatic ring carboxylic acid which may be substituted with a carboxylic acid group, and the amino group acylated with a heteroaromatic ring carboxylic acid which may be substituted with a carboxylic acid group represented by $R^2$ or $R^3$ are each independently selected from the group consisting of a formylamino group, an acetylamino group, a propionylamino group, a butyrylamino group, a benzoylamino group, a naphthoylamino group, a pyridinecarbonylamino group, a pyrrolecarbonylamino group, a carboxyacetylamino group, a carboxypropionylamino group, a carboxybutyrylamino group, a carboxybenzoylamino group, a carboxynaphthoylamino group, a carboxypyridinecarbonylamino group, and a carboxypyrrolecarbonylamino group.

48. A method according to claim 28, wherein the amino group sulfonylated with a $C_1$ to $C_4$ lower alkanesulfonic acid which may be substituted with a carboxylic acid group, the amino group sulfonylated with an aromatic ring sulfonic acid which may be substituted with a carboxylic acid group, and the amino group sulfonylated with a heteroaromatic ring sulfonic acid which may be substituted with a carboxylic acid group represented by $R^2$ or $R^3$ are each independently selected from the group consisting of a methanesulfonylamino group, an ethanesulfonylamino group, a propanesulfonylamino group, a benzenesulfonylamino group, a naphthalenesulfonylamino group, a pyridinesulfonylamino group, a pyrrolesulfonylamino group, a carboxymethanesulfonylamino group, a carboxyethanesulfonylamino group, a carboxypropanesulfonylamino group, a carboxybenzenesulfonylamino group, a carboxynaphthalenesulfonylamino group, a carboxypyridine-sulfonylamino group, and a carboxypyrrolesulfonylamino group.

49. A method according to claim 28, wherein the fused heterocyclic ring which may be substituted with a carboxylic acid and in which the carbon atom in the ring may form a carbonyl group which $R^1$ and $R^2$ form together with the substituting benzene ring when the ring A is a benzene ring, is selected from the group consisting of a tetrahydroquinoline, a benzoxazine, a quinoxaline, a benzodioxane, a carboxytetrahydroquinoline, a carboxybenzoxazine, a carboxyquinoxaline, and a carboxybenzodioxane.

50. A method according to claim 28, wherein the $C_1$ to $C_4$ lower alkyl group represented by X is selected from the group consisting of a methyl group, an ethyl group, a n-propyl group, a n-butyl group, an isopropyl group, a sec-butyl group, and a t-butyl group.

51. A method according to claim 28, wherein the $C_1$ to $C_4$ lower alkoxyl group represented by X is selected from the group consisting of a methoxy group, an ethoxy group, a n-propyloxy group, a n-butoxy group, an isopropyloxy group, a sec-butoxy group, and a t-butoxy group.

52. A method according to claim 28, wherein the halogen atom represented by X, is selected from the group consisting of a fluorine atom, a chlorine atom, a bromine atom and an iodine atom.

53. A method according to claim 28, wherein the pharmaceutically acceptable salt is selected from the group consisting of an acid salt and an alkali metal salt.

54. A method according to claim 53, wherein the pharmaceutically acceptable salt is selected from the group consisting of a hydrochloric acid salt, a methanesulfonic acid salt, a trifluoroacetic acid salt, a sodium salt and a potassium salt.

* * * * *